US009546210B2

(12) United States Patent
Vale et al.

(10) Patent No.: US 9,546,210 B2
(45) Date of Patent: Jan. 17, 2017

(54) CRIPTO ANTAGONISM OF ACTIVIN AND TGF-B SIGNALING

(75) Inventors: Wylie Vale, La Jolla, CA (US); Craig A. Harrison, Nunswading (AU); Peter C. Gray, San Diego, CA (US)

(73) Assignee: Research Development Foundation, Carson City, NV (US)

( * ) Notice: Subject to any disclaimer, the term of this patent is extended or adjusted under 35 U.S.C. 154(b) by 1453 days.

(21) Appl. No.: 12/887,272

(22) Filed: Sep. 21, 2010

(65) Prior Publication Data

US 2011/0009319 A1 Jan. 13, 2011

Related U.S. Application Data

(62) Division of application No. 10/940,431, filed on Sep. 14, 2004, now Pat. No. 7,820,620.

(60) Provisional application No. 60/503,046, filed on Sep. 15, 2003.

(51) Int. Cl.
| | |
|---|---|
| *A61K 38/18* | (2006.01) |
| *C07K 16/22* | (2006.01) |
| *C07K 14/47* | (2006.01) |
| *C07K 14/475* | (2006.01) |
| *C07K 14/71* | (2006.01) |
| *C07K 14/82* | (2006.01) |

(52) U.S. Cl.
CPC .............. *C07K 16/22* (2013.01); *C07K 14/47* (2013.01); *C07K 14/475* (2013.01); *C07K 14/71* (2013.01); *C07K 14/82* (2013.01)

(58) Field of Classification Search
None
See application file for complete search history.

(56) References Cited

U.S. PATENT DOCUMENTS

| | | | |
|---|---|---|---|
| 5,792,616 A | 8/1998 | Persico et al. | 435/7.21 |
| 5,854,399 A | 12/1998 | Salomon et al. | 530/387.7 |
| 7,297,478 B1 | 11/2007 | Reinl et al. | 435/6 |
| 2001/0036635 A1 | 11/2001 | Waldman et al. | 435/6 |
| 2005/0255117 A1 | 11/2005 | Sanicola-Nadel et al. | 424/155.1 |

FOREIGN PATENT DOCUMENTS

| | | |
|---|---|---|
| WO | WO 94/11502 | 5/1994 |
| WO | WO 02/22808 | 3/2002 |
| WO | WO 02/077033 | 10/2002 |
| WO | WO 02/088170 | 11/2002 |
| WO | WO 03/083041 | 10/2003 |
| WO | WO 2004/083375 | 9/2004 |

OTHER PUBLICATIONS

Tanimoto et al., Biochemical and Biophysical Research Communications 259, 699-705 (1999).*
Brown et al., Nat Genet. Aug. 2000;25(4):453-7.*
de Krester et al., Molecular and Cellular Endocrinology 225 (2004) 57-64.*
Schnepp et al., Cancer Biol Ther. Mar.-Apr. 2003;2(2):171-2.*
MacPherson et al., Journal of Endocrinology (1997) 154, 535-545.*
Vassalli et al., Genes Dev. 8, 414-427 (1994).*
Extended European Search Report issued in issued in European Patent application No. 09009758.5, dated Aug. 27, 2010.
Office Communication issued in Australian Patent Application No. 2004274433, dated May 25, 2010.
Office Communication issued in Australian Patent Application No. 2004274433, dated Jan. 20, 2010.
Office Communication issued in European Patent Application No. 04783979.0, dated Jun. 2, 2008.
Office Communication issued in Japanese Patent Application No. 2006-526968, dated Jul. 29, 2010. (English translation).
PCT International Search Report and Written Opinion issued in International application No. PCT/US04/29967, dated Oct. 31, 2009.
Office Communication, issued in Canadian Patent Application No. 2,539,116, dated May 24, 2011.
Adkins et al., "Antibody blockade of the Cripto CFC domain suppresses tumor cell growth in vivo," *The Journal of Clinical Investigation*, 112(4):575-578, 2003.
Attisano et al., "Identification of human activin and TGFBETA type I receptors that form hetermeric kinase complexes with type II receptors," *Cell*, 75:671-680, 1993.
Attwood, "The Babel of Bioinformatics," *Science*, 290:471-473, 2000.
Brand, "The Diagnosis of Pancreatic Cancer," *Focus on Pancreatic Cancer*, 7(4):287-97, 2001.
Cheng et al., "EGF-CFC proteins are essential coreceptors for the TGF-β signals Vg1 and GDF1," *Genes and Development*, 17:31-36, 2003.
Dijke et al., "Activin receptor-like kinases: A novel subclass of cell-surface receptors with predicted serine/threonine kinase activity," *Oncogene*, 8(10):2879-2887, 1993.
Fawcett et al., "Mapping the Homotypic Binding Sites in CD31 Adhesion in the Formation of Interendothelial Cell Contacts," *The Journal of Cell Biology*, 128(6):1229, 1995.
Genbank accession No. Z22536, Feb. 10, 1999.
Gray et al., "Cripto Binds Transforming Growth Factor β (TGF-β) and Inhibits TGF-β Signaling," *Molecular and Cellular Biology*, 26(24):9268-9278, 2006.
Gray et al., "Cripto forms a complex with activin and type II activin receptors and can block activin signaling," *Proceedings of the National Academy of Sciences of the United States of America*, 100(9):5193-5198, 2003.

(Continued)

Primary Examiner — Zachary Skelding
(74) Attorney, Agent, or Firm — Parker Highlander PLLC

(57) ABSTRACT

Cripto, a developmental oncoprotein, antagonizes activin and TGF-b signaling by forming a complex with activin and TGF-b and their type II receptors. This complex precludes the formation of a functional activin/TGF-b•type II•type I complex, thereby blocking the signaling of activin and TGF-b. Cripto may be generally capable of blocking antiproliferative Smad2/3 signals and provides a novel mechanism of oncogenic action with multiple therapeutic implications. Inhibiting the formation of Cripto and activin/TGF-b complex may enhance antiproliferative effects of activin and TGF-b.

20 Claims, 13 Drawing Sheets

(56) References Cited

OTHER PUBLICATIONS

Harrison et al., "An Activin Mutant with Disrupted ALK4 Binding Blocks Signaling via Type II Receptors," *The Journal of Biolgical Chemistry*, 279(27):28036-28044, 2004.

Harrison et al., "Antagonists of activin signaling: mechanisms and potential biological applications," *Trends in Endocrinology and Metabolism*, 16:73-78, 2005.

Harrison et al., "Identification of a Functional Binding Site for Activin on the Type 1 Receptor ALK4*" *Journal of Biological Chemistry*, 278(23):21129-21135, 2003.

Jakowlew, "Transforming growth factor—β in cancer and metastais," *Cancer Metastasis Rev*, 25:435-457, 2006.

Javelaud et al., "Stable overexpression of Smad7 in human melanoma cells inhibits their tumorigenicity in vitro and in vivo," *Oncogene*, 24:7624-7629, 2005.

Kelber et al., "Cripto is a non-competitive activin antagonist that forms analogous signaling complexes with activin and nodal," *Journal of Biological Chemistry*, 283:4490-4500, 2008.

Mathews, "Activin receptors and cellular signaling by the receptor serine kinase family," *Endocrine Reviews*, 15(3):310-325, 1994.

Ngo et al., "Computational Complexity, Protein Structure Prediction and the Levinthal Paradox," in *The Protein Folding Problem and Tertiary Structure Prediction*, Mertz et al. (ed.), Birkhauser, Boston, MA, 433, 492-495, 1994.

Office Communication issued in U.S. Appl. No. 10/940,431, mailed on Nov. 30, 2005.

Office Communication issued in U.S. Appl. No. 10/940,431, mailed on Apr. 25, 2006.

Office Communication issued in U.S. Appl. No. 10/940,431, mailed on Jan. 17, 2007.

Office Communication issued in U.S. Appl. No. 10/940,431 mailed on Jan. 10, 2008.

Office Communication issued in U.S. Appl. No. 10/940,431, mailed on Oct. 3, 2008.

Office Communication issued in U.S. Appl. No. 10/940,431, mailed on Jun. 11, 2009.

Office Communication issued in U.S. Appl. No. 10/940,431, mailed on Apr. 16, 2010.

Partial European Search Report, issued in European Patent application No. 09009758.5, dated May 10, 2010.

Rebbapragada et al., "Myostatin Signals through a Transforming Growth Factor β-Like Signaling Pathway to Block Adiopogenesis," *Molecular and Cellular Biology*, 23(20):7230-7242, 2003.

Risbridger et al., "The contribution of inhibins and activins to malignant prostate disease," *Molecular and Cellular Endocrinology*, 180:149-153, 2001.

Schiffer et al., "Fucosylation of cripto is required for its ability to facilitate nodal signaling," *The Journal of Biological Chemistry*, 276(41):37769-37778, 2001.

Shen, "Decrypting the role of *Cripto* in tumorigenesis," *Journal of Clinical Investigation*, 112(4)500-502, 2003.

Skolnick et al., "From genes to protein structure and function: novel applications of computational approaches in the genomic era," *Trends in Biotechnology*, 18:34-39, 2000.

Supplementay European Search Report, issued in European Application No. EP04783979, dated Feb. 22, 2008.

Suzuki et al., "Soluble Type II Transforming Growth Factor-β Receptor Inhibits Establishe Murine Malignant Mesothelioma Tumor Growth," *Clinical Cancer Research*, 10:5907-5918, 2004.

Wojtowicz-Praga, "Reversal of tumor induced immunosuppression by TGF-β inhibitors," *Investigational New Drugs*, 21:21-32, 2003.

Yan et al., "Dual roles of cripto as a ligand and coreceptor in the nodal signaling pathway," *Molecular and Cellular Biology*, 22(13):4439-4449, 2002.

Yeo and Whitman, "Nodal signals to Smads through cripto-dependent and cripto-independent mechanisms," *Molecular Cell*, 7:949-957, 2001.

Office Communication, issued in Japanese Patent Application No. 2006-526968, dated Oct. 24, 2011. (English translation).

Corrigan et al., "Evidence for an autocrine role of activin B within rat anterior pituitary cultures," *Endocrinology*, 128:1682-1684, 1991.

Mirthrprabhu et al., "Activin bioactivity affects germ cell differentiation in the postnatal mouse testis in vivo," *Biology of Reprod.*, 82:980-990,2010.

\* cited by examiner

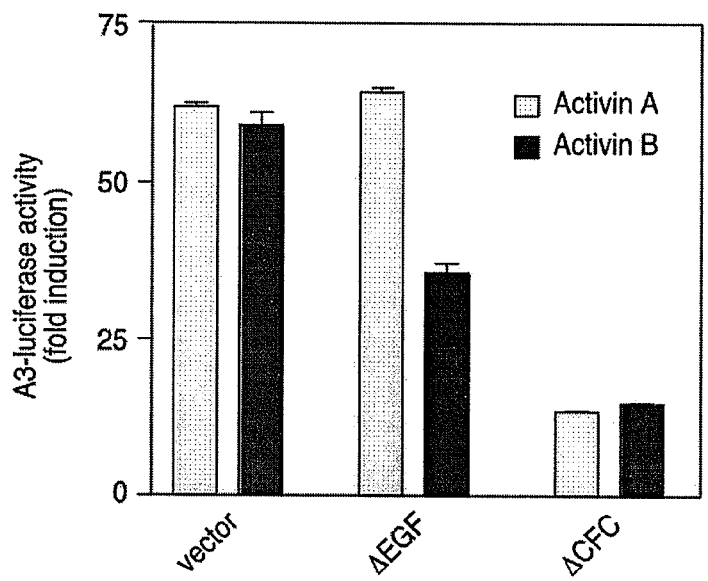
Fig. 10
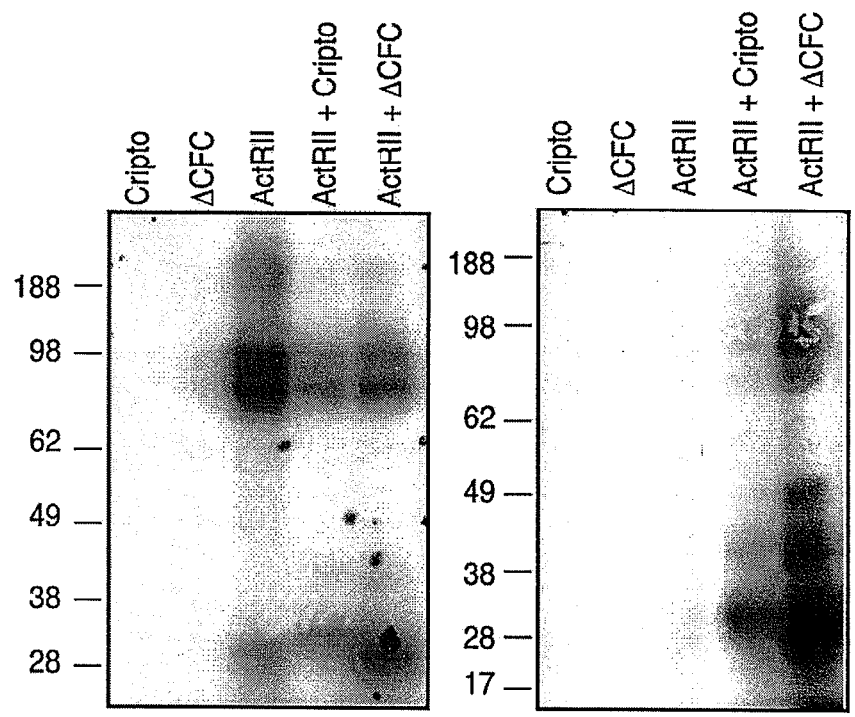
IP: anti-ActRII (myc)   IP: anti-Cripto (Flag)
Fig. 11A            Fig. 11B

Fig. 15

SEQUENCE LISTING

<160> NUMBER OF SEQ ID NOS: 6

<210> SEQ ID NO 1
<211> LENGTH: 171
<212> TYPE: PRT
<213> ORGANISM: Mus musculus

<400> SEQUENCE: 1

```
Met Gly Tyr Phe Ser Ser Val Val Leu Leu Val Ala Ile Ser Ser
1               5                   10                  15

Ala Phe Glu Phe Gly Pro Val Ala Gly Arg Asp Leu Ala Ile Arg Asp
                20                  25                  30

Asn Ser Ile Trp Asp Gln Lys Glu Pro Ala Val Arg Asp Arg Ser Phe
            35                  40                  45

Gln Phe Val Pro Ser Val Gly Ile Gln Asn Ser Lys Ser Leu Asn Lys
        50                  55                  60

Thr Cys Cys Leu Asn Gly Gly Thr Cys Leu Leu Gly Ser Phe Cys Ala
65                  70                  75                  80

Cys Pro Pro Ser Glu Tyr Gly Arg Asn Cys Glu His Asp Val Arg Lys
                85                  90                  95

Glu His Cys Gly Ser Ile Leu His Gly Thr Trp Leu Pro Lys Lys Cys
                100                 105                 110

Ser Leu Cys Arg Cys Trp His Gly Gln Leu His Cys Leu Pro Gln Thr
            115                 120                 125

Phe Leu Pro Gly Cys Asp Gly His Val Met Asp Gln Asp Leu Lys Ala
        130                 135                 140

Ser Arg Thr Pro Cys Gln Thr Pro Ser Val Thr Thr Thr Phe Met Leu
145                 150                 155                 160

Ala Gly Ala Cys Leu Phe Leu Asp Met Lys Val
165                 170
```

<210> SEQ ID NO 2
<211> LENGTH: 188
<212> TYPE: PRT
<213> ORGANISM: Homo sapiens

<400> SEQUENCE: 2

```
Met Asp Cys Arg Lys Met Ala Arg Phe Ser Tyr Ser Val Ile Trp Ile
1               5                   10                  15

Met Ala Ile Ser Lys Val Phe Glu Leu Gly Leu Val Ala Gly Leu Gly
                20                  25                  30

His Gln Glu Phe Ala Arg Pro Ser Arg Gly Tyr Leu Ala Phe Arg Asp
            35                  40                  45
```

```
Asp Ser Ile Trp Pro Gln Glu Glu Pro Ala Ile Arg Pro Arg Ser Ser
    50                  55                  60

Gln Arg Val Pro Pro Met Gly Ile Gln His Ser Lys Glu Leu Asn Arg
65                  70                  75                  80

Thr Cys Cys Leu Asn Gly Gly Thr Cys Met Leu Gly Ser Phe Cys Ala
                85                  90                  95

Cys Pro Pro Ser Phe Tyr Gly Arg Asn Cys Glu His Asp Val Arg Lys
            100                 105                 110

Glu Asn Cys Gly Ser Val Pro His Asp Thr Trp Leu Pro Lys Lys Cys
            115                 120                 125

Ser Leu Cys Lys Cys Trp His Gly Gln Leu Arg Cys Phe Pro Gln Ala
    130                 135                 140

Phe Leu Pro Gly Cys Asp Gly Leu Val Met Asp Glu His Leu Val Ala
145                 150                 155                 160

Ser Arg Thr Pro Glu Leu Pro Pro Ser Ala Arg Thr Thr Thr Phe Met
                165                 170                 175

Leu Val Gly Ile Cys Leu Ser Ile Gln Ser Tyr Tyr
                180                 185
```

<210> SEQ ID NO 3
<211> LENGTH: 202
<212> TYPE: PRT
<213> ORGANISM: Mus musculus

<400> SEQUENCE: 3

```
Met Arg Ala Asn Ser Pro Thr Gln Gly Ile Ser Leu Lys Met His Gln
1               5                   10                  15

Ala Arg Pro Leu Phe Leu Val Thr Val Ala Leu Gln Leu Ile Gly Leu
                20                  25                  30

Gly Tyr Ser Tyr Gln Ser Glu Gly Asp Gly Ala Arg Glu Val Ser Asn
            35                  40                  45

Ile Leu Ser Pro Val Ile Pro Gly Thr Thr Leu Asp Arg Thr Leu Ser
    50                  55                  60

Asn Ser Ser Arg Lys Asn Asp Ile Pro Glu Gly Ala Arg Leu Trp Asp
65                  70                  75                  80

Ser Leu Pro Asp Ser Ser Thr Leu Gly Glu Ser Ala Val Pro Val Ser
                85                  90                  95

Arg Cys Cys His Asn Gly Gly Thr Cys Val Leu Gly Ser Phe Cys Val
            100                 105                 110

Cys Pro Ala Tyr Phe Thr Gly Arg Tyr Cys Glu His Asp Gln Arg Arg
            115                 120                 125

Arg Asp Cys Gly Ala Leu Gly His Gly Ala Trp Thr Leu His Ser Cys
    130                 135                 140

Arg Leu Cys Arg Cys Ile Phe Ser Ala Leu Tyr Cys Leu Pro His Gln
145                 150                 155                 160

Thr Phe Ser His Cys Asp Leu Lys Ser Phe Leu Ser Ser Gly Ala Arg
                165                 170                 175

Gly Ser Arg Glu Cys Ser Ile Pro Ser Leu Leu Leu Val Leu Cys
            180                 185                 190

Leu Leu Leu Gln Gly Val Ala Gly Lys Gly
            195                 200
```

<210> SEQ ID NO 4
<211> LENGTH: 223
<212> TYPE: PRT

<213> ORGANISM: Homo sapiens

<400> SEQUENCE: 4

```
Met Thr Trp Arg His His Val Arg Leu Leu Phe Thr Val Ser Leu Ala
1               5                   10                  15
Leu Gln Ile Ile Asn Leu Gly Asn Ser Tyr Gln Arg Glu Lys His Asn
            20                  25                  30
Gly Gly Arg Glu Glu Val Thr Lys Val Ala Thr Gln Lys His Arg Gln
        35                  40                  45
Ser Pro Leu Asn Trp Thr Ser Ser His Phe Gly Glu Val Thr Gly Ser
    50                  55                  60
Ala Glu Gly Trp Gly Pro Glu Pro Leu Pro Tyr Ser Arg Ala Phe
65                  70                  75                  80
Gly Glu Gly Ala Ser Ala Arg Pro Arg Cys Cys Arg Asn Gly Gly Thr
                85                  90                  95
Cys Val Leu Gly Ser Phe Cys Val Cys Pro Ala His Phe Thr Gly Arg
            100                 105                 110
Tyr Cys Glu His Asp Gln Arg Ser Glu Cys Gly Ala Leu Glu His
        115                 120                 125
Gly Ala Trp Thr Leu Arg Ala Cys His Leu Cys Arg Cys Ile Phe Gly
    130                 135                 140
Ala Leu His Cys Leu Pro Leu Gln Thr Pro Asp Arg Cys Asp Pro Lys
145                 150                 155                 160
Asp Phe Leu Ala Ser His Ala His Gly Pro Ser Ala Gly Ala Pro
                165                 170                 175
Ser Leu Leu Leu Leu Pro Cys Ala Leu Leu His Arg Leu Leu Arg
            180                 185                 190
Pro Asp Ala Pro Ala His Pro Arg Ser Leu Val Pro Ser Val Leu Gln
        195                 200                 205
Arg Glu Arg Arg Pro Cys Gly Arg Pro Gly Leu Gly His Arg Leu
    210                 215                 220
```

<210> SEQ ID NO 5
<211> LENGTH: 190
<212> TYPE: PRT
<213> ORGANISM: Xenopus laevis

<400> SEQUENCE: 5

```
Met Gln Phe Leu Arg Phe Leu Ala Ile Leu Ile Phe Ser Ala Lys His
1               5                   10                  15
Phe Ile Lys His Cys Lys Gly Glu Thr Cys Met Gly Leu Asn Cys Asn
            20                  25                  30
Asp Pro Gly Leu Leu Glu Ala Ile Lys Ser Asn Thr Ile Asn Gln Leu
        35                  40                  45
Leu His Asp Thr Ile Asn Ala Thr His Gly Lys Ser Pro Ala Lys Ser
    50                  55                  60
Thr Lys Thr Leu Pro Phe Leu Gly Ile Thr Asp Ser Lys Lys Leu Asn
65                  70                  75                  80
Arg Lys Cys Cys Gln Asn Gly Gly Thr Cys Phe Leu Gly Thr Phe Cys
                85                  90                  95
Ile Cys Pro Lys Gln Phe Thr Gly Arg His Cys Glu His Glu Arg Arg
            100                 105                 110
Pro Ala Ser Cys Ser Gly Val Pro His Gly Asp Trp Ile Thr Gln Gly
        115                 120                 125
Cys Leu Leu Cys Arg Cys Val Ser Gly Val Leu His Cys Phe Lys Pro
```

```
                130                135                140
Glu Ser Glu Asp Cys Asp Val Val His Glu Lys Asn Met Arg Ser Gly
145                150                155                160

Val Pro Arg Met Gln Leu Ser Leu Ile Ile Tyr Cys Phe Leu Thr Ala
                165                170                175

Asn Leu Phe Tyr His Ile Val Trp His Leu Asn Ile Gly Leu
                180                185                190

<210> SEQ ID NO 6
<211> LENGTH: 190
<212> TYPE: PRT
<213> ORGANISM: Brachydanio rerio

<400> SEQUENCE: 6

Met Thr Ser Gln Leu Phe Gly Phe Leu Met Phe Ala Val Ile Ile Cys
1               5                  10                 15

Gln Ala Val Ser Leu Glu Ser Gly Cys Glu Gly Ser Glu Cys Val Lys
                20                 25                 30

Val Gly Val Ser Gly Lys Pro Lys Gln Tyr Ala Glu Phe Leu Asn Lys
                35                 40                 45

Phe Asn Glu Met Asn Thr Gln Thr Pro Gln Arg Gln His Arg Asn Ala
            50                 55                 60

Glu Ala Ala Leu Pro Phe Val Gly Leu Thr Gly Val Ala Lys Gln Ser
65                 70                 75                 80

Arg Thr Cys Cys Lys Asn Gly Gly Thr Cys Ile Leu Gly Ser Phe Cys
                85                 90                 95

Ala Cys Pro Lys Tyr Phe Thr Gly Arg Ser Cys Glu Tyr Asp Glu Arg
                100                105                110

Leu Arg Asp Cys Gly Val Ile Pro His Gly Glu Trp Val Gln Lys Gly
                115                120                125

Cys Ser Tyr Cys Arg Cys Gly Tyr Gly Leu Leu His Cys Phe Pro His
                130                135                140

Val Phe Ser Lys Asp Cys Asp Val Phe Ser Lys Asp Cys Asp Asp Ser
145                150                155                160

Gln Glu Val Arg Trp His Arg Ser Gly Ser Leu Arg Thr Leu Ser Ser
                165                170                175

Thr Ile Val Met Phe Ala Thr Phe Ile Leu His Arg Leu Leu
                180                185                190
```

CRIPTO ANTAGONISM OF ACTIVIN AND TGF-B SIGNALING

CROSS-REFERENCE TO RELATED APPLICATION

This application is a divisional application of currently pending U.S. application Ser. No. 10/940,431, filed Sep. 14, 2004, which claims the benefit of provisional patent application Ser. No. 60/503,046, filed Sep. 15, 2003. The entire text of each of the above-referenced disclosures is specifically incorporated herein by reference without disclaimer.

BACKGROUND OF THE INVENTION

Field of the Invention

The present invention relates generally to signaling of TGF-b superfamily. More specifically, the present invention relates to antagonism of signaling of TGF-b superfamily ligands.

Description of the Related Art

The transforming growth factor b (TGF-b) superfamily comprise over 30 secreted ligands in human that control cell growth, homeostasis, differentiation, tissue development, immune responses, angiogenesis, wound repair, endocrine function and many other physiologic processes. Members of this superfamily include TGF-b, activins, bone morphogenetic protein (BMP), Growth and Differentiation Factor (GDF) and nodal-related families. Disruption or dysregulation of activin and TGF-b signaling is associated with multiple pathological states including carcinogenesis.

TGF-b superfamily members share a distinct structural framework known as the cystine knot scaffold. Activin and TGF-b are each disulfide-linked dimmers. Activin consists of two b chains. Although there are several activin b subunit genes and an extensive array of possible b-b dimers, only bA-bA (activin-A), bA-bB (activin-AB) and bB-bB (activin-B) have been isolated as dimeric proteins and shown to be biologically active. Three TGF-b genes exist in mammals giving rise to the $TGF-b_1$, $TGF-b_2$ and $TGF-b_3$ isoforms.

Activin and TGF-b Signaling Via Receptor Serine Kinases

TGF-bs, activins and other members of the TGF-b superfamily exert their biological effects by interacting with two types of transmembrane receptors (type I and type II) with intrinsic serine/threonine kinase activities, called receptor serine kinases (RSKs). Type I receptor serine kinases are referred to as ALK1 to 7, for Activin receptor-Like Kinases. The receptor activation mechanism was first established for TGF-b which was shown to bind its type II receptor (TbRII) leading to the recruitment, phosphorylation and activation of its type I receptor (ALK5). A similar mechanism of ligand-mediated receptor assembly and type I receptor phosphorylation has been demonstrated for activin receptors involving initial binding of activin to ActRII or ActRIIB followed by recruitment, phosphorylation and activation of the type I receptor ALK4.

The ligand binding properties of the receptor extracellular domains (ECDs) have been extensively examined. The crystal structure of the ActRII-ECD provided detailed information regarding sites predicted to be involved in receptor: ligand interactions. The crystal structure of the ActRII-ECD bound to BMP-7 has recently been solved and it was shown that the amino acids on ActRII required for activin-A binding make up interfacial contacts between ActRII and BMP-7 and are required for BMP-7 binding. An allosteric conformational change was observed in BMP-7 in its predicted type I receptor binding site following binding to ActRII. This suggested a general model for cooperative type I/type II receptor assembly induced by BMPs (or activin) to form a hexameric complex containing the dimeric ligand, two type II receptors and two type I receptors.

The structure of activin-A bound to the ActRIIB-ECD was also solved recently and was generally consistent with previous findings regarding the activin-A binding site on the ActRIIA receptor. Using the crystal structure of BMP2 bound to the BMP type I receptor (ALK3-ECD) as a guide, an activin-A binding surface on the type I receptor ALK4-ECD was recently identified.

The structure of $TGF-b_3$ bound to the TbRII-ECD has also been solved and indicated unexpectedly that the TGF-b binding interface with its type II receptor is very different from the corresponding interface of activin and BMP7 with ActRII. This suggests that although activin and TGF-b have a similar mechanism of receptor activation, they apparently have unrelated ligand-type II receptor interfaces.

Regardless of the precise mechanism of receptor assembly by TGF-b superfamily ligands, it has been generally established that following receptor assembly, type II receptors phosphorylate type I receptors within a juxtamembrane cytoplasmic glycine- and serine-rich region called the GS domain and this phosphorylation event activates the type I receptor kinase to initiate downstream signaling.

Regulation of Activin And TGF-b Receptor Access

Activins are secreted in their processed, biologically active form. However, the ability of activins to access and assemble signaling receptors can be inhibited in several distinct ways. Inhibins (a-b) share a b subunit with activins and are TGF-b superfamily members that act in conjunction with the membrane proteoglycan betaglycan to form high affinity complexes with activin type II receptors, thereby preventing these receptors from binding activin and initiating signaling. The soluble, extracellular activin binding follistatins bind activins with high-affinity and also block the ability of activin to bind its cell-surface receptors and initiate signaling. In addition, the pseudo (decoy) type I receptor BAMBI (BMP and Activin Membrane-Bound Inhibitor) can bind BMP or activin in non-functional complexes with activin and BMP receptors to block signaling.

Unlike activin, TGF-b isoforms are not secreted in an active form but rather are secreted as inactive "latent" complexes. These complexes comprise the inactive TGF-b dimer in non-covalent complexes with two prosegments to which one of several "latent TGF-b binding proteins" is often linked. Latent TGF-b complexes and their binding proteins associate with the extracellular matrix and await one of several possible activating stimuli to provide a rapidly available pool of releasable TGF-b that can respond to highly localized signals.

Smad Signaling

Based upon genetic studies in *Drosophila* and *Caenorhabditis elegans*, a group of proteins now called Smads have been found to transduce signals from receptor serine kinases and mediate regulation of target gene transcription by activin, TGF-b and other TGF-b superfamily members. Structural and functional considerations allow subdivision of Smads into three subfamilies: pathway-specific, common mediator, and inhibitory Smads.

Ligand/receptor assembly and activin receptor-like kinase (ALK) phosphorylation triggers a transient ALK/pathway-specific Smad association during which the ALK phosphorylates the Smad on its last two serine residues in the C terminal SSXS motif. Activin and TGF-b signals are mediated by the pathway-specific Smads, Smad2 and Smad3 and these Smads are sequestered near their signaling receptors by Smad Anchor for Receptor Activation (SARA), a cytoplasmic membrane-associated protein that has been shown to facilitate Smad2/3 signaling.

Once activated, Smad2 and Smad3 form hetero-oligomeric complexes with the common mediator Smad, Smad4, that was first discovered in humans as the pancreatic tumor suppressor gene, DPC4. Smad2/3/4 complexes translocate to the nucleus and interact directly with DNA and/or with cell-type specific co-activator or co-repressor proteins leading to the activation or repression of target genes.

Two vertebrate inhibitory Smads have been identified, Smad6 and 7, which lack the C-terminal SSXS motif found in the pathway specific Smads. Smad6 and 7 are inhibitors of Smad signaling and bind to activin receptor-like kinases (ALKs) to prevent phosphorylation and activation of the pathway-specific Smads. In transfected cells, Smad7 inhibits transcriptional responses induced by activin or TFG-b or by a constitutively active ALK4. Smad7 may therefore provide an intracellular feedback signal to restrain the effects of activin and TFG-b.

Smad2/3 Signaling and Growth Control

TGF-b and activin are both well known for their ability to inhibit proliferation of multiple cell types including most epithelial cells, and gene expression profiling has indicated essential similarity of transcriptional responses to constitutively active activin or TGF-b type I receptors in cancer cells. Activation of the Smad2/3 signaling pathway leads to inhibition of cell cycle progression during G1 and in some cases terminal differentiation, or apoptosis. The growth inhibitory response to Smad2/3 signals has been divided into two major classes: gene responses that lead to inhibition of cyclin-dependent kinases (cdks) and down regulation of c-myc.

The retinoblastoma tumor suppressor protein (pRb) and its family members p107 and p130 control cell cycle progression and have activity that is regulated by cdk phosphorylation. TGF-b signals have been shown to induce cdk inhibitors including $p15^{INK4B}$ (p15) and $p21^{CIP1/WAF1}$ (p21) and to down regulate the tyrosine phosphatase cdc25A. p15 binds and inactivates cdk4 and cdk6 causing displacement of p27 from cyclin D-cdk4/6, allowing it to bind and inhibit cyclin E-cdk2. p21 also binds and inhibits cyclin E-cdk2. cdc25A is an activator of cyclin D-cdk4 and its down regulation therefore reduces the activity of this cdk. Overall, decreased cdk activity in response to Smad2/3 signaling reduces pRb phosphorylation by these cdks, allowing pRb to prevent E2F function and block cell cycle progression.

Unlike cdk inhibition, which exhibits cell type dependent diversity, down regulation of c-Myc, a member of the basic helix-loop-helix leucine zipper (bHLH-LZ) family of transcription factors, is observed in most cell types that are growth inhibited by Smad2/3 signals. In addition, down regulation of c-Myc by Smad signals is required for the inactivation of cdks, and evidence also implicates c-Myc as a positive regulator of cdc25A expression. It was recently shown that E2F4/5 proteins and the Rb protein p107 form a pre-formed complex with Smad3 in the cytoplasm that awaits TGF-b receptor activation, Smad3 phosphorylation and Smad4 assembly leading to translocation of the complex to the nucleus to bind the c-myc promoter and repression of the c-myc gene.

The Id family of transcriptional regulators inhibit terminal differentiation, promote cell proliferation and have been implicated in cancer. Myc and Id proteins can form complexes that cooperate to override the tumor suppressor function of pRb. Interestingly, it was recently shown that TGF-b causes repression of Id gene expression via preassembled, cytoplasmic Smad3-ATF3 complexes that translocate to the nucleus with Smad4 and target Id promoters following TGF-b receptor activation. It was also recently demonstrated that key cellular responses to TGF-b signals, including induction of the cdk inhibitor p21, rely on direct interactions between Smad2 and the tumor suppressor and transcriptional regulator p53. In summary, these results indicate that Smad2 and Smad3 likely play essential but distinct roles in regulating cell proliferation.

Smad2/3 Pathway and Cancer

It is not surprising that disruptions or alterations in the activin and TGF-b signaling pathways have been observed in several types of human cancer. Inactivating mutations in TbRII have been observed in colorectal and gastric carcinomas and inactivation of ActRII was recently observed in gastrointestinal cancers. An inactivating mutation in TbRI (ALK5) occurs in one third of ovarian cancers observed and ALK4 mutations have been described in pancreatic cancer leading to the designation of ALK4 as a tumor suppressor gene.

The activin/TGF-b signaling pathway is also disrupted by mutations in Smad4 and Smad2. As mentioned above, Smad4 was originally identified as DPC4 (deleted in pancreatic carcinoma locus 4) and this gene is functionally absent in half of all pancreatic cancers and one third of colon carcinomas. Smad2 is also inactivated in a small proportion of colorectal cancers and lung cancers. Although Smad3 mutations have not yet been observed in human cancers, $Smad3^{-/-}$ mice developed colorectal cancer.

Interestingly, despite its antiproliferative effects, Smad2/3 signaling can also exacerbate the cancer phenotype under conditions in which cells have become refractory to Smad2/3-induced growth inhibition. For example, increased production of TGF-b or activin by tumor cells that are no longer growth inhibited by Smad2/3 signals may lead to increased angiogenesis, decreased immune surveillance and/or an increase in the epithelial to mesenchymal transition (EMT) of tumor cells. Collectively, these effects can lead to increased tumor growth and metastasis.

Epidermal Growth Factor-Cripto, FRL-1, Cryptic (EGF-CFC) Protein Family

Similar to activin, members of the nodal family and GDF-1/Vg1 have been shown to signal via the activin receptors ActRII/IIB and ALK4. Unlike activin, however, these TGF-b superfamily members require additional co-receptors from the Epidermal Growth Factor-Cripto, FRL-1, Cryptic (EGF-CFC) protein family to assemble type II and type I receptors and generate signals.

The EGF-CFC family consists of small, glycosylated, extracellular signaling proteins including human and mouse Cripto and Cryptic, *Xenopus* FRL-1 and zebrafish one-eyed pinhead (oep). EGF-CFC proteins are known to act as anchored cell surface co-receptors but they also have activity when expressed as soluble proteins or when they are secreted from the cell surface following enzymatic cleavage of their GPI anchor. Genetic studies in zebrafish and mice have shown that EGF-CFC proteins are required for mesoderm and endoderm formation, cardiogenesis, and the establishment of left/right asymmetry during embryonic development. Cripto knockout mouse embryos lack a primitive streak and fail to form embryonic mesoderm. This phenotype is very similar to that observed in $ActRIIA^{-/-}$; $ActRIIB^{-/-}$ mice, $ALK4^{-/-}$ mice and $Nodal^{-/-}$ mice, consistent with a requirement for nodal signaling via activin receptors and a role for Cripto to initiate primitive streak elongation and mesoderm formation. It has been shown that Cripto independently binds nodal via its EGF-like domain and ALK4 via its CFC domain. Furthermore, selected point mutations in Cripto that block nodal binding or ALK4 binding disrupt nodal signaling. Substantial biochemical evidence indicates that nodal and Vg1/GDF1 form a complex with activin receptors only in the presence of EGF-CFC proteins.

Cripto is a Tumor Growth Factor

Cripto is an EGF-CFC protein that was first isolated as a putative oncogene from a human teratocarcinoma cell line and it was subsequently shown to be able to confer anchorage independent growth to NOG-8 mouse mammary epithelial cells. Cripto is expressed at high levels in human breast, colon, stomach, pancreas, lung, ovary, endometrial, testis, bladder and prostate tumors while being absent or expressed at low levels in their normal counterparts. The elucidation of the signals and transcriptional events underlying the high level of Cripto expression in these tumors remains an important area of future research.

With regard to Cripto's mechanism(s) of mitogenic action, it has been shown that recombinant, soluble Cripto and a synthetic 47 amino acid Cripto fragment spanning the EGF-like domain can activate both the mitogen activated protein kinase (MAPK) pathway and the phosphatidylinositol-3-kinase (PI3K) pathway. Treatment of HC-11 mammary epithelial cells with soluble Cripto or the 47-mer peptide resulted in tyrosine phosphorylation of the SH2-adaptor protein Shc, association of Shc with Grb2 and activation of the p42/44 Erk/MAPK pathway. It was also shown that soluble Cripto caused phosphorylation of the p85 regulatory subunit of PI3K leading to phosphorylation and activation of AKT in SiHa cervical carcinoma cells. Cripto does not bind to members of the EGF receptor family, although $[^{125}I]$-Cripto specifically labeled breast cancer cell lines and formed crosslinked complexes with 60 kDa and 130 kDa membrane proteins. Although these proteins were not identified, the 60 kDa protein may have been ALK4.

It was recently shown that the cytoplasmic tyrosine kinase c-Src can be activated by soluble Cripto and that its activity is required for activation of the MAPK/PI3K pathways by Cripto. The GPI-anchored proteoglycan glypican was also reported to be important in facilitating these Cripto signals and glypican was also shown to bind Cripto in a manner dependent on glycanation of glypican. The ability of Cripto to activate the MAPK and PI3K pathways, which are frequently growth-stimulatory in nature, has generally been proposed to explain Cripto's oncogenic effects.

Smad Signaling, Cripto and Cancer

The first demonstration of a physiologic role for TGF-b was its potent and reversible inhibition of developing mouse mammary gland in situ. TGF-b is now well established as an important inhibitor of mammary ductal growth and branching in vivo and over 90% of mammary carcinomas are ductal in nature. Loss of TbRII has been associated with increased risk of invasive breast cancer in women. Consistent with a role in regulating mammary ductal growth, TGF-$b_1$ heterozygous null mice display accelerated mammary epithelial proliferation and ductal outgrowth. Furthermore, transgenic expression of a dominant negative TbRII construct in mammary gland diminishes responsiveness to TGF-b and caused increased incidence of tumors in response to carcinogen relative to control mice. Conversely, transgenic overexpression of TGF-$b_1$ in mammary gland protects against chemical-induced tumors. These results provide direct evidence that TGF-b signaling can actively prevent tumorigenesis in mouse mammary gland. There is also evidence that activin inhibits proliferation of both primary and transformed mammary epithelial cells. Together, these results indicate the importance of the Smad2/3 pathway in inhibiting mammary epithelial cell proliferation and tumorigenesis.

Cripto is overexpressed in many types of human tumors, including ~80% of breast carcinomas, while its expression is low or absent in their normal counterparts. In contrast to TGF-b, Cripto promotes growth in mammary cells and Cripto overexpression transforms mouse NOG-8 and CID-9 mammary epithelial cells. Cripto overexpression in these cell lines enabled them to grow in soft agar and each displayed an enhanced proliferation rate in monolayer culture. These cells were, however, unable to form tumors in nude mice.

It was also shown that targeted disruption of endogenous Cripto in CID-9 cells via a retroviral antisense construct led to a decreased rate of cellular proliferation. Both the soluble Cripto protein and the 47 amino acid EGF-like domain Cripto peptide have also been shown to facilitate ductal branching and cause mammary ductal hyperplasia. As discussed above, these effects have been explained as the result of the ability of Cripto to activate mitogenic signaling pathways including the MAPK and PI3K pathways. However, many of the growth-related effects of Cripto are also generally consistent with antagonism of the Smad2/3 pathway.

The prior art is lacking in evidence on whether Cripto can play a dual role as an oncogene, not only acts by activating mitogenic MAPK/PI3K pathways, but also antagonizes the antiproliferative Smad2/3 pathway. The present invention thus studies the oncogenic mechanism of Cripto protein in order to gain insight into its effects on activin/TGF-b signaling.

SUMMARY OF THE INVENTION

TGF-b and activin regulate tissue homeostasis by activating the Smad2/3 intracellular signaling pathway leading to potent inhibition of proliferation of multiple cell types including epithelial cells. Disruption of this signaling pathway is associated with oncogenesis and tumorigenesis. Cripto is a developmental oncoprotein that is highly expressed in human tumors but not their normal tissue counterparts. Overexpression of Cripto transforms mammary epithelial cells in vitro. The present invention shows that Cripto can antagonize activin and TGF-b signaling. These results suggest that Cripto may be generally capable of blocking antiproliferative Smad2/3 signals and provides a novel mechanism of oncogenic action with multiple therapeutic implications.

Based on the data presented below, a model for the mechanism of Cripto regulation of activin and TGF-b signaling is proposed (FIG. 13). In the absence of Cripto, activin and TGF-b signal by binding their respective type II receptors and then recruiting their type I receptors (ALK4 and ALK5). Activin and TGF-b type II receptors phosphorylate the GS domain of ALK4 and ALK5, thereby activating the type I kinase and initiating downstream signaling. Cripto antagonizes activin and TGF-b signaling by forming a complex with activin and TGF-b and their type II receptors. This complex precludes the formation of a functional activin/TGF-b•type II•type I complex and therefore blocks signaling.

In one embodiment of the present invention, there is provided a method of augmenting signaling of a ligand of receptor serine kinase in a cell. The method involves inhibiting the formation of complexes between Cripto and a ligand of receptor serine kinase on the surface of a cell.

In another embodiment, there is provided a method of using a mutant of a ligand of receptor serine kinase to augment Smad2/3 signaling in a cell.

The present invention also provides a method of using a Cripto mutant that lacks the EGF domain to selectively antagonize activin-B signaling.

In another embodiment, there is provided a method of inhibiting signaling of a ligand of receptor serine kinase in a cell. The method involves enhancing the formation of complexes between Cripto and a ligand of receptor serine kinase on the surface of a cell.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

FIG. 5A is a diagram of mouse Cripto indicating the positions of the signal peptide, N-terminal FLAG epitope, EGF-like domain, CFC domain and the C-terminal site of GPI-anchor attachment. In addition, the site of fucosylation (threonine 72) and the positions of the tryptophan residues that are substituted with glycine residues in the mCFC mutant (W104G, W107G) are indicated. (B) Empty vector or the indicated Cripto constructs were transfected in triplicate into 293T cells and the resulting cell surface expression of these constructs in intact cells was measured using anti-FLAG antibody in an ELISA-based assay (FIG. 5B).

FIG. 10 shows the EGF-like and CFC domains of Cripto can independently mediate antagonism of activin-B signaling. 293T cells were transfected in triplicate with vector, Cripto DEGF or Cripto DCFC in addition to A3-luciferase/FAST-2/CMV-b-galactosidase. Cells were treated with vehicle or with either 300 pM activin-A or 300 pM activin-B as indicated, and resulting luciferase activities were normalized and presented as the fold-increase relative to b-galactosidase activities in vehicle-treated cells.

FIGS. 11A-B show Cripto DCFC mutant binds activin-A. 293T cells were transfected with the indicated constructs and subjected to crosslinking with [$^{125}$I]-activin-A. Solubilized, crosslinked complexes were isolated by immunoprecipitation using anti-myc antibody targeting ActRII (FIG. 11A) or anti-FLAG antibody targeting Cripto (FIG. 11B). Immunoprecipitated proteins were resolved by SDS-PAGE and visualized by autoradiography.

Figure 13A:
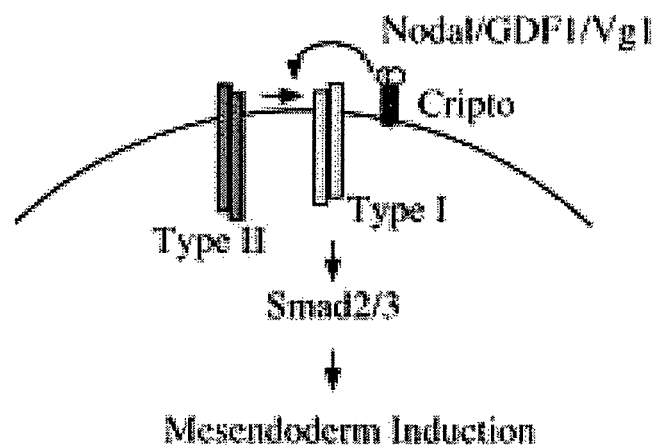
FIGS. 13A-B depict proposed mechanisms of Cripto regulation of TGF-b ligand signaling. The model illustrates the ability of Cripto to either facilitate (FIG. 13A) or inhibit (FIG. 13B) signaling of TGF-b superfamily members.
Figure 13B:
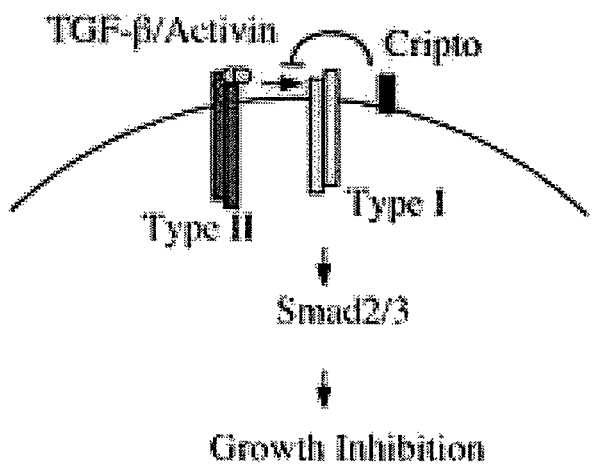

Cripto and related Epidermal Growth Factor-Cripto, FRL-1, Cryptic (EGF-CFC) protein family proteins bind directly to nodal or Vg1/GDF1, allowing these ligands to assemble type II and type I signaling receptors and initiating responses including mesoderm induction (FIG. 13A). Conversely, by binding TGF-b and activin while these ligands are in complex with their respective type II receptors, Cripto disrupts functional recruitment of type I receptors and inhibits signaling responses such as growth inhibition (FIG. 13B).

Figure 14:
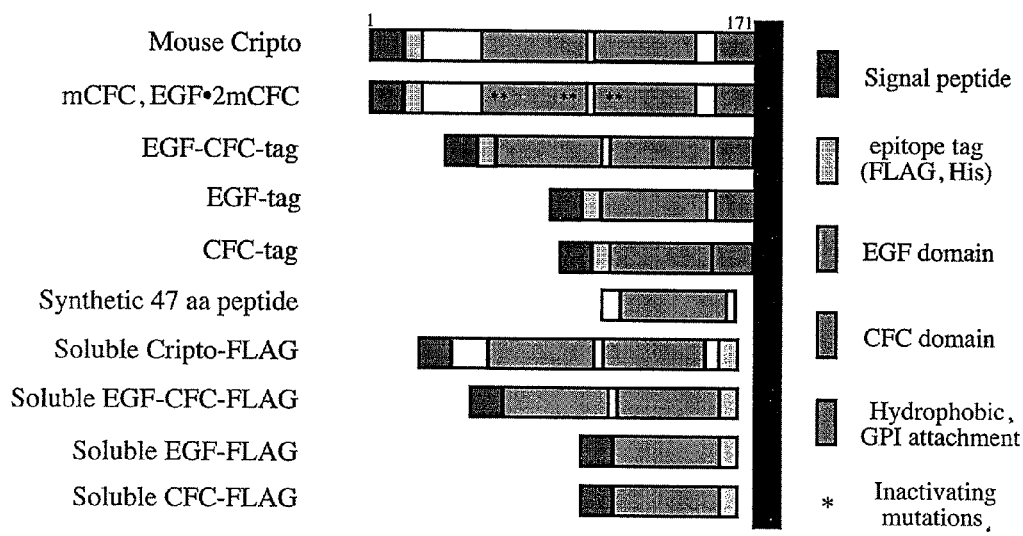

FIG. 14 depict diagrams of Cripto and Cripto mutant constructs. The domain structure of wild type mouse Cripto is indicated showing attachment to membrane via C-terminal GPI anchorage. Position of incorporated epitope tags and sites of deletions and selected mutations are indicated.

Figure 15:
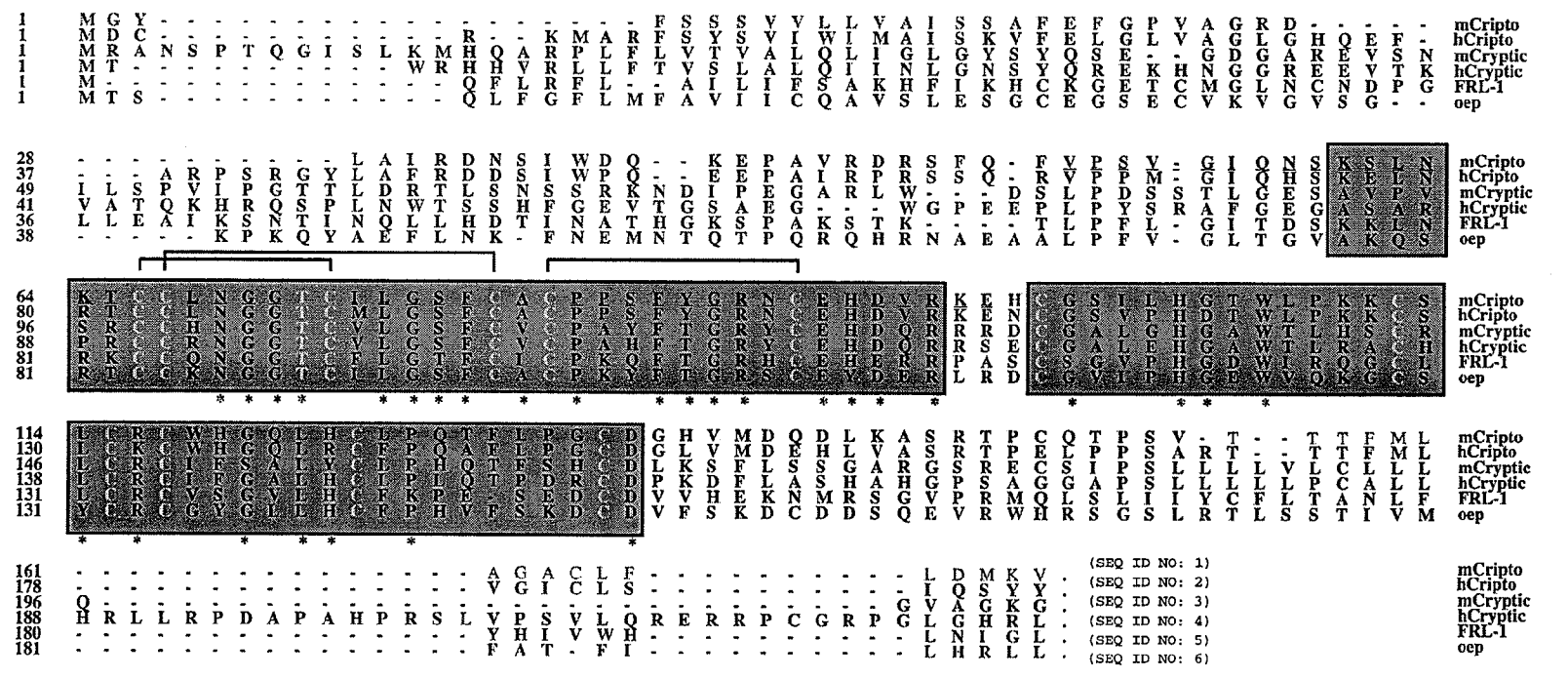

FIG. 15 shows alignment of Epidermal Growth Factor-Cripto, FRL-1, Cryptic (EGF-CFC) proteins. Mouse Cripto was aligned with other members of the EGF-CFC family including human Cripto, mouse Cryptic, human Cryptic, *Xenopus* FRL-1 and zebrafish one-eyed pinhead (oep) using the CLUSTAL algorithm of the MEGALIGN program (DNASTAR). The EGF-like domain is boxed and shaded red, the CFC domain is boxed and shaded blue, and conserved cysteines within these domains are shaded yellow. Disulfide arrangement of the EGF-like domain is indicated. The signal peptide of mouse Cripto is indicated with red lettering, the hydrophobic C-terminal domain is indicated with purple lettering and the fucosylated threonine is shaded white. Conserved residues targeted for mutagenesis are indicated by asterisks and the EGF1, EGF2 and mCFC mutations are indicated by red asterisks.

DETAILED DESCRIPTION OF THE INVENTION

The present invention provides methods of augmenting signaling induced by a ligand of receptor serine kinase in a cell by inhibiting the formation of complexes between Cripto and the receptor serine kinase ligand on the surface of the cell. Ligands of receptor serine kinase include, but are not limited to, activin and TGF-b, whereas examples of receptor serine kinase include type I activin receptor-like kinases-4 (ALK-4) or activin receptor-like kinases-5 (ALK-5). In general, the cells are derived from breast, colon, stomach, pancreas, lung, ovary, endometrial, testis, bladder or prostate. Augmentation of signaling mediated by receptor serine kinase would increase phosphorylation and activation of Smad2 and Smad3, resulting in decreased cellular proliferation.

In one embodiment, formation of complexes between Cripto and ligand of receptor serine kinase is inhibited by an anti-Cripto antibody directed against an epitope of Cripto. For example, the anti-Cripto antibody is directed against an epitope in the EGF-like domain of Cripto. Alternatively, formation of complexes between Cripto and receptor serine kinase ligand can be inhibited by a soluble receptor serine kinase extracellular domain that binds Cripto but not ligand of receptor serine kinase. In one embodiment, the soluble extracellular domain is an activin receptor-like kinases-4 (ALK-4) extracellular domain. Preferably, the ALK-4 extracellular domain comprises a mutation at one or more positions such as amino acid position 70, 75 and/or 77. For example, the ALK-4 extracellular domain comprises an alanine at amino acid position 70, 75 and/or 77.

In another embodiment, formation of complexes between Cripto and ligand of receptor serine kinase is inhibited by inhibiting the expression of Cripto in the cell. Cripto expression can be inhibited by antisense transcript of Cripto, small inhibitory RNA (siRNA) directed against Cripto or by mutating at least one allele of Cripto by homologous recombination.

In yet another embodiment, there is provided a method of using a mutant of a ligand of receptor serine kinase to augment Smad2/3 signaling in a cell. The mutant ligand retains signaling activity but is unable to bind to Cripto, thereby bypassing antagonism by Cripto. In general, ligands of receptor serine kinase include, but are not limited to, activin and TGF-b.

The present invention also provides a method of using a Cripto mutant that lacks the EGF domain to selectively antagonize activin-B signaling. In general, the Cripto mutant can be soluble or cell surface-bound. Results disclosed herein show that the EGF-like domain of Cripto is required to antagonize activin-A, activin-B and TGF-b while the CFC domain is sufficient to block activin-B but not activin-A or TGF-b. Therefore Cripto mutant that lacks the EGF domain will be a useful research tool to distinguish the relative importance of activin-A as opposed to activin-B signaling in various biological contexts. For example, it has also been previously demonstrated that release of FSH from rat anterior pituitary gonadotropes is mediated by activin-B. Therefore, a Cripto mutant such as DEGF is predicted to block FSH release without affecting activin-A or TGF-b signaling. By blocking FSH release, spermatogenesis will be disrupted potentially causing reversible infertility. Therefore, cell attached or soluble Cripto constructs in which the EGF-like domain has been deleted may have utility as male contraceptives.

The present invention further provides a method of inhibiting signaling induced by a ligand of receptor serine kinase in a cell by enhancing the formation of complexes between Cripto and the receptor serine kinase ligand on the surface of the cell. Ligands of receptor serine kinase include, but are not limited to, activin and TGF-b, whereas examples of receptor serine kinase include type I activin receptor-like kinases-4 (ALK-4) or activin receptor-like kinases-5 (ALK-5). In general, the cells are derived from breast, colon, stomach, pancreas, lung, ovary, endometrial, testis, bladder or prostate. In one embodiment, formation of complexes between Cripto and ligand of receptor serine kinase is enhanced by increasing the expression of Cripto in the cell. For example, Cripto expression can be increased by administering to the cell viral or plasmid vectors that encodes Cripto protein. Alternatively, formation of complexes between Cripto and receptor serine kinase ligand can be enhanced by administering soluble Cripto or cell surface-bound Cripto to the cell.

The following examples are given for the purpose of illustrating various embodiments of the invention and are not meant to limit the present invention in any fashion. The present examples, along with the methods, procedures, treatments, molecules, and specific compounds described herein are presently representative of preferred embodiments. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

Example 1

Figure 1:
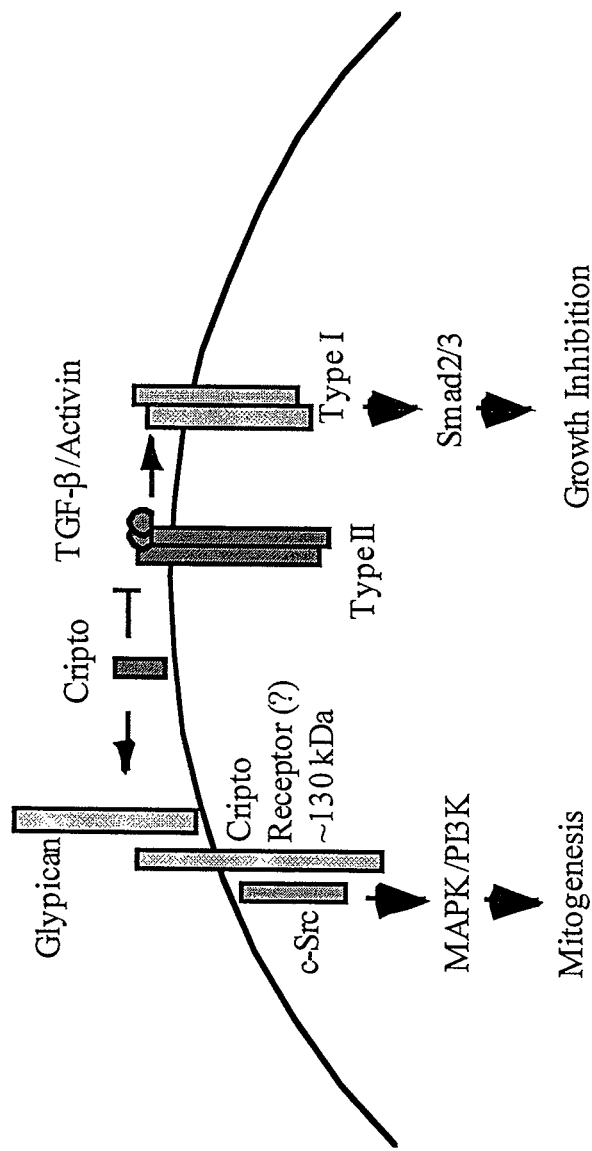
FIG. 1 shows a model indicating the proposed dual oncogenic mechanisms of Cripto. Cripto activates mitogenic MAPK and PI3K pathways by binding an as-yet uncharacterized transmembrane receptor leading to activation of c-Src. It is proposed that Cripto also blocks Smad2/3 signaling by competitively antagonizing functional recruitment of type I activin and TGF-b receptors to ligand•type II receptor complexes.
Figure 2:
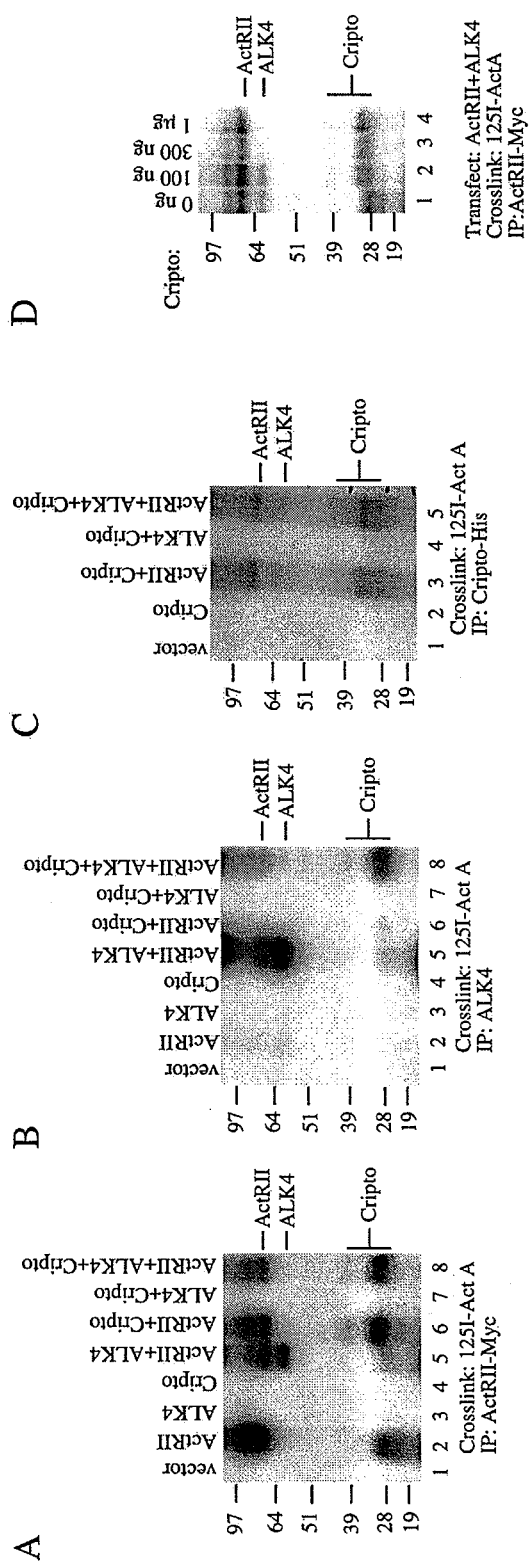
FIG. 2 shows Cripto binds activin in the presence of ActRII and competes with ALK4 for activin•ActRII binding. 293T cells were transfected with the indicated constructs and subjected to crosslinking with [$^{125}$I]-activin-A as previously described (Gray et al., 2003). The cells were solubilized and crosslinked complexes were isolated by immunoprecipitation using the indicated antibodies. Immunoprecipitated proteins were resolved by SDS-PAGE and visualized by autoradiography as previously described (Gray et al., 2003).

Cripto Binds Activin in the Presence of ActRII and Competes with ALK4 for Activin•ActRII Binding The ability of [$^{125}$I]-activin-A to form crosslinked complexes with Cripto was tested in the presence or absence of activin receptors. FIG. 2 shows that when 293T cells were transfected with ActRII (FIG. 2A, lane 2) and then subjected to labeling and crosslinking with [$^{125}$I]-activin-A followed by immunoprecipitation with an antibody directed against ActRII, an activin-ActRII crosslinked complex of ~80 kDa was evident consistent with previous crosslinking results. The appearance of two ActRII•activin bands is routinely observed and is likely the result of differential glycosylation of ActRII.

Co-transfection of ActRII with ALK4 (FIG. 2A, lane 5) results in crosslinking of [$^{125}$I]-activin-A to both receptor types as indicated by the appearance of the activin•ALK4 crosslinked complex at ~60 kDa. No binding of [$^{125}$I]-activin-A to Cripto was detected in the absence of activin type II receptors (FIG. 2C, lane 2). However, when ActRII was co-transfected with Cripto, activin-crosslinked complexes of ~32, 45 and 52 kDa were observed (FIG. 2A, lane 6). These complexes were not present in samples in which Cripto was not transfected (lanes 1-3, 5; the ~28 kDa band represents crosslinked [$^{125}$I]-activin-A dimer). The Cripto species of ~18, 31 and 38 kDa (the activin bA monomer is ~14 kDa and the gels were run under reducing conditions) likely have differential glycosylation and/or other modifications.

The presence of [$^{125}$I]-activin-A•Cripto bands indicates the formation of stable activin•ActRII•Cripto complexes since an antibody directed against ActRII was used in the immunoprecipitation. Activin•ActRII and activin•Cripto crosslinked bands were also evident when 293T cells were co-transfected with ActRII and Cripto and then subjected to immunoprecipitation using an antibody directed against Cripto (FIG. 2C, lanes 3 and 5).

The effects of co-transfecting 293T cells with Cripto, ActRII and ALK4 were further tested. When Cripto was transfected with ActRII and ALK4 (FIG. 2A, lane 8), [$^{125}$I]-activin-A formed a crosslinked complex with ActRII and Cripto, while crosslinking to ALK4 was greatly decreased relative to crosslinking in the absence of Cripto (FIG. 2A, compare lane 5 and lane 8). Co-transfection with Cripto did not decrease expression of ALK4 as shown by Western blot (data not shown).

The effects of Cripto on activin•ActRII•ALK4 complex formation as assessed following immunoprecipitation with an antibody directed against ALK4. FIG. 2B shows that when 293T cells were transfected with vector (FIG. 2B, lane 1), ActRII (FIG. 2B, lane 2), ALK4 (FIG. 2B, lane 3), Cripto (FIG. 2B, lane 4) or co-transfected with ActRII and Cripto (FIG. 2B, lane 6) or ALK4 and Cripto (FIG. 2B, lane 7) and then subjected to crosslinking with [$^{125}$I]-activin-A, an ALK4 antibody failed to isolate labeled complexes. This is consistent with the inability of either Cripto or ALK4 to bind [$^{125}$I]-activin-A in the absence of type II receptors. When ActRII and ALK4 were co-expressed, the anti-ALK4 antibody precipitated a complex in which both ActRII and ALK4 were labeled (FIG. 2B, lane 5).

Co-transfection of Cripto with ActRII and ALK4 substantially blocked the appearance of these bands (FIG. 2B, lane 8), consistent with its ability to block crosslinking of activin to ALK4 and the association of ALK4 with ActRII. However, when ActRII, ALK4 and Cripto were co-transfected and cells were labeled with [$^{125}$I]-activin-A, the ALK4 antibody could precipitate labeled [$^{125}$I]-activin-A•Cripto complexes (FIG. 2B, lane 8).

Cripto blocks labeling and crosslinking of [$^{125}$I]-activin-A to ALK4 in a dose dependent manner. FIG. 2D shows that as the amount of transfected Cripto DNA is increased, the ability of [$^{125}$I]-activin-A to crosslink to ALK4 decreases. These results provide a mechanism for competitive antagonism of activin signaling by Cripto.

Example 2

Figure 3:
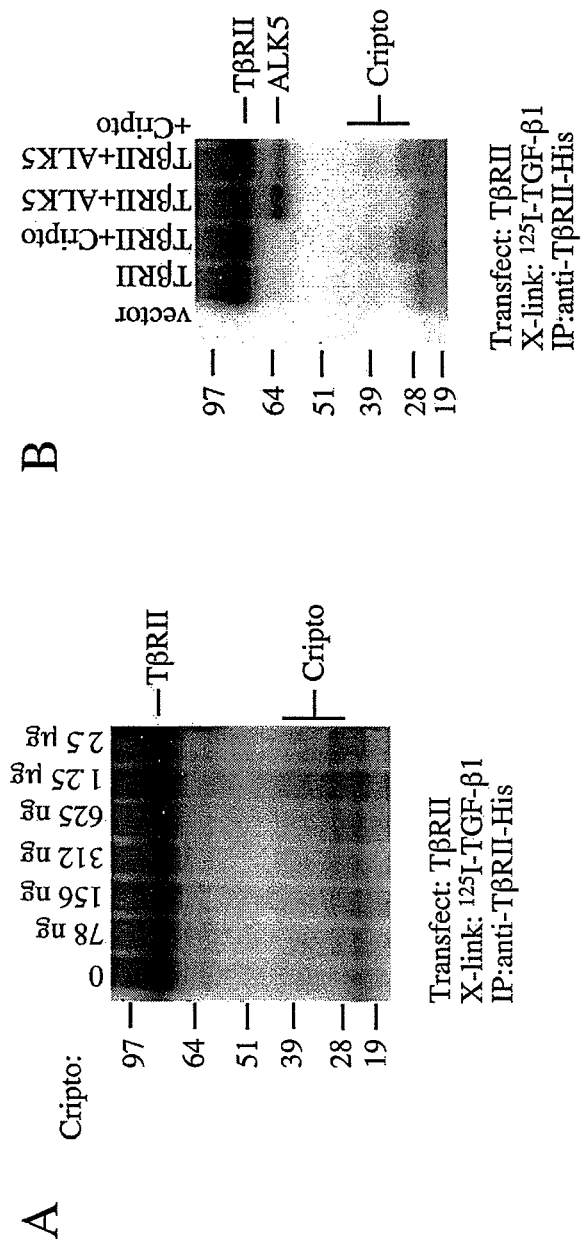
FIG. 3 shows Cripto binds TGF-$b_1$ in the presence of TbRII and competes with ALK5 for TGF-$b_1$•TbRII binding. 293T cells were transfected with the indicated constructs and subjected to crosslinking with [$^{125}$I]-TGF-$b_1$ as previously described (Gray et al., 2003). The cells were solubilized and crosslinked complexes were isolated by immunoprecipitation using the indicated antibodies. Immunoprecipitated proteins were resolved by SDS-PAGE and visualized by autoradiography as previously described (Gray et al., 2003).

Cripto Binds TGF-b$_1$ in the Presence of TbRII and Competes with ALK5 for TGF-b$_1$•TbRII Binding Similar to activin-A, TGF-b1 binds Cripto in the presence of its type II receptor TbRII. FIG. 3A shows crosslinking of [$^{125}$I]-TGF-b$_1$ to 293T cells transfected with TbRII and the indicated amounts of Cripto DNA. A prominent [$^{125}$I]-TGF-b$_1$•Cripto crosslinked band of ~32 kDa appeared and increased in intensity as the amount of Cripto DNA transfected was increased. Fainter species of •40 kDa were also visible (FIG. 3A).

The effects of Cripto on the ability of [$^{125}$I]-TGF-b$_1$ to crosslink to its type I receptor ALK5 were examined. FIG. 3B shows that [$^{125}$I]-TGF-b$_1$ forms a crosslinked complex with its type II receptor of ~85 kDa (FIG. 3B, lane 2) and that co-transfection of Cripto with TbRII results in the [$^{125}$I]-TGF-b$_1$•TbRII complex as well as the [$^{125}$I]-TGF-b$_1$•Cripto complex. When TbRII and ALK5 were co-transfected, [$^{125}$I]-TGF-b$_1$ labeled both receptors to yield complexes of ~85 kDa and 60 kDa respectively (FIG. 3B, lane 4). When TbRII, ALK5 and Cripto were co-transfected, all three bands were evident (FIG. 3B, lane 5). However, the intensity of the ALK5 band was reduced, indicating Cripto may compete with ALK5 for available TGF-b•TbRII binding sites.

Example 3

Cripto Blocks Activin-A and TGF-b$_1$ Signaling in HepG2 Cells

Figure 4:
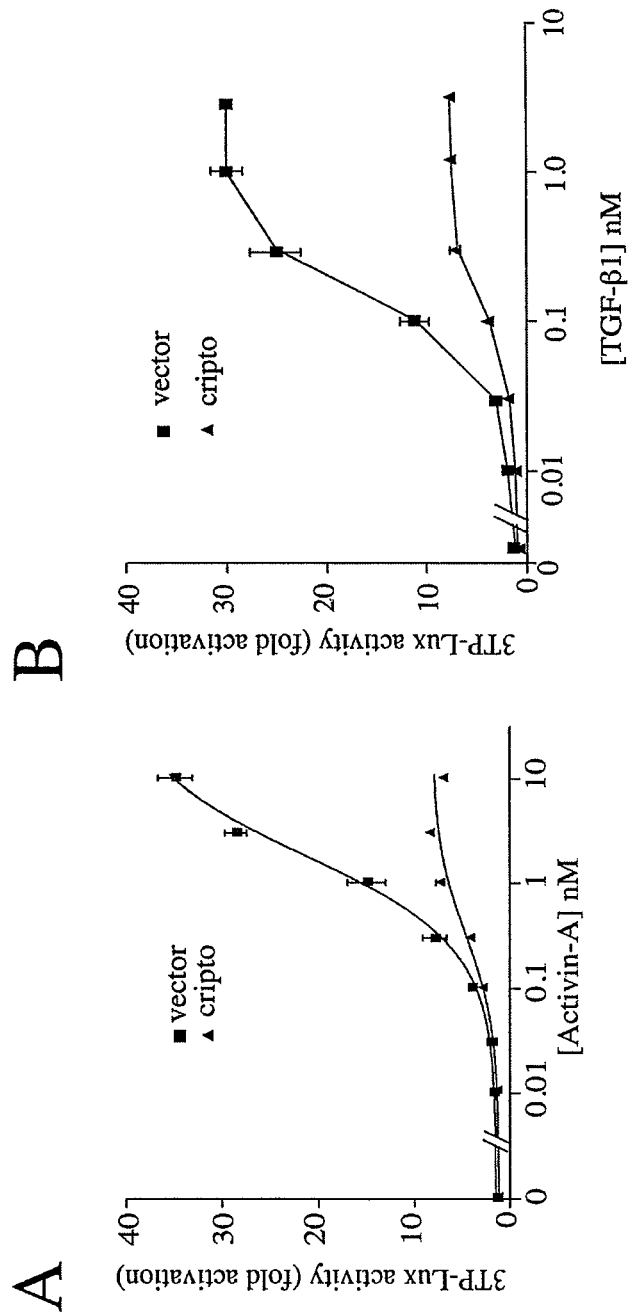
FIG. 4 shows Cripto blocks activin-A and TGF-$b_1$ signaling in HepG2 cells. HepG2 cells were transfected with either empty vector or Cripto as previously described (Gray et al., 2003) and then treated with the indicated doses of either activin-A (FIG. 4A) or TGF-$b_1$ (FIG. 4B). Luciferase activities were normalized relative to b-galactosidase activities and data were presented as fold increases in luciferase activity relative to untreated cells.

HepG2 cells do not express Cripto and require transfected Cripto to respond to nodal signals. Therefore, the effects of transfected Cripto on activin-A and TGF-b$_1$ signaling were tested in this cell line. Cripto and the activin/TGF-b responsive luciferase reporter construct 3TP-lux were transfected into HepG2 cells and the effect of Cripto on activin-A and TGF-b$_1$-induced luciferase expression was measured. As shown in FIG. 4, activin-A and TGF-b$_1$ caused dose-dependent increases in luciferase expression that were inhibited by Cripto. At maximal doses of these ligands there was an approximately four-fold reduction in signaling (FIG. 4A, B). As a control, the effect of Cripto on the ability of the activin-A paralog BMP7 to induce luciferase expression using the BMP-selective reporter BRE-luc has previously been tested. Although BMP7 induced luciferase expression in HepG2 cells in a dose-dependent manner, Cripto did not affect this induction, indicating that Cripto's effects may be selective for activin, TGF-b and the Smad2/3 pathway (Gray et al., 2003).

Example 4

Expression of Cripto Mutants at the Cell Surface of 293T Cells

Figure 5A:
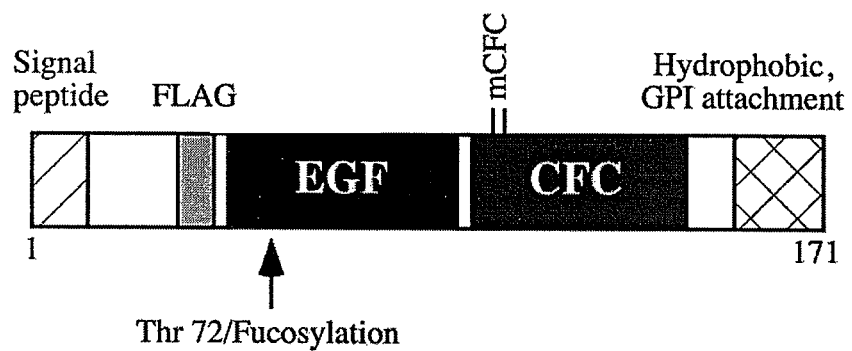
FIGS. 5A-B show expression of Cripto mutants at the cell surface of 293T cells.

The domain structure of mouse Cripto is illustrated in FIG. 5A. This diagram indicates the locations of the signal peptide, the EGF-like domain, the CFC domain and the C-terminal hydrophobic region required for GPI-anchor attachment. In addition, the positions of the FLAG epitope, the fucosylated threonine residue (Thr 72), and the mCFC mutations (H104G, W107G) (Yeo and Whitman, 2001) are shown.

Five Cripto constructs were evaluated in this study: wild type Cripto; Cripto (T72A), which is unable to be fucosylated and does not facilitate nodal signaling; Cripto DEGF, in which the EGF-like domain has been deleted; Cripto mCFC, which does not facilitate nodal signaling and has two mutations in the CFC domain that block ALK4 binding (H104G, W107G); and Cripto DCFC, in which the CFC domain has been deleted.

Figure 5B:
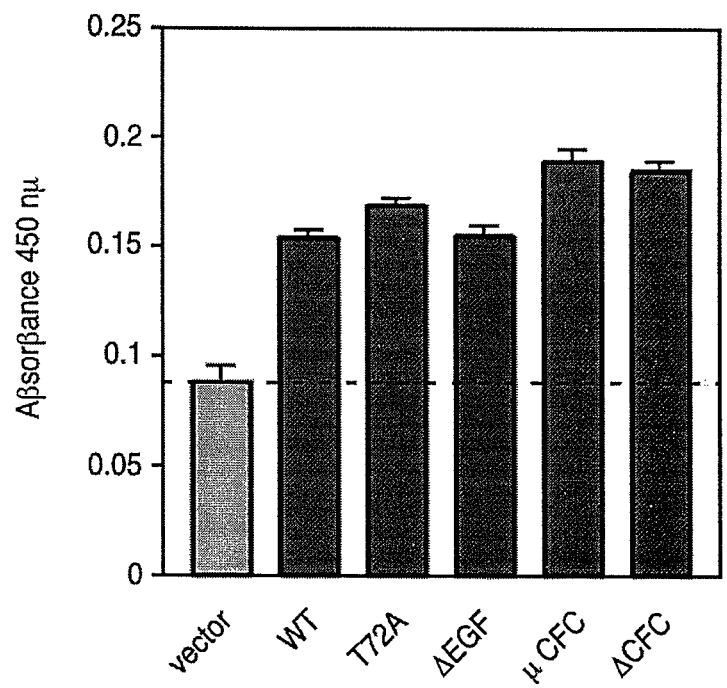

Cell surface expression levels of wild type Cripto and these four Cripto mutants are shown in FIG. 5B. 293T cells were transfected with the indicated Cripto constructs and cell surface expression was subsequently measured using anti-FLAG antibody in an intact cell ELISA-based assay that we have previously used to measure expression levels of cell surface proteins (Harrison et al., 2003). Briefly, 293T cells were plated on 24 well polylysine-coated plates at a density of 100,000 cells per well; transfected 24 h later with 0.5 mg vector or Cripto DNA per well and then assayed for cell surface expression 48 h after transfection. Cells were rinsed in Hepes Dissociation Buffer (HDB) (12.5 mM Hepes (pH 7.4), 140 mM NaCl and 5 mM Kcl), fixed in 4% paraformaldehyde for 30 min at 4° C., rinsed with HDB and then incubated in HDB with 3% bovine serum albumin (BSA) for 30 min at room temperature (RT). Cells were then incubated for 2 h with 2 µg/ml anti-Myc antibody in HDB with 3% BSA, rinsed with HDB, and incubated with peroxidase-conjugated anti-mouse IgG in HDB with 3% BSA for 1 h at room temperature. Wells were rinsed with HDB and then 100 µl of TMB peroxidase substrate was added to each well. Plates were incubated at RT until the solutions turned visibly blue. Peroxidase activity was stopped by adding 100 µl of 0.18 M $H_2SO_4$ to each well and peroxidase activity was quantified by measuring the absorbance of the resulting yellow solutions at 450 nm.

As shown in FIG. 5B, these Cripto constructs were expressed at cell surface at similar levels.

Example 5

The EGF-Like Domain of Cripto is Required for Antagonism of Activin-A and TGF-b Signaling Like other Epidermal Growth Factor-Cripto, FRL-1, Cryptic (EGF-CFC) protein family members, Cripto has two conserved cysteine-rich domains, an N-terminal EGF-like domain and a C-terminal CFC domain. Each of these modular domains can have activity in the absence of the other and both have been implicated in specific protein-protein interactions and signaling functions. To determine the roles of the Cripto EGF-like and CFC domains in blocking TGF-b signaling, we compared the ability of wild type Cripto to inhibit TGF-b with that of Cripto mutants in which either the EGF-like or CFC domain was mutated or deleted.

Luciferase assays were carried out essentially as previously described (Gray et al., 2003). HepG2 cells were plated at 150,000 cells per well in 24-well plates and transfected in triplicate approximately 24 h later with 1 mg DNA per well with a ratio of 800 ng Cripto/100 ng 3TP-lux/100 ng cytomegalovirus (CMV)-b-galactosidase (CMV-b-galactosidase). Cells were treated with TGF-$b_1$ approximately 30 h after transfection and harvested 16 h following treatment. Cells were incubated in solubilization buffer (1% Triton X-100, 25 mM glycylglycine (pH 7.8), 15 mM $MgSO_4$, 4 mM EGTA and 1 mM DTT) for 30 min on ice and luciferase reporter activity was measured and normalized relative to CMV-b-gal activities. 293T cells were plated on 24-well plates treated with polylysine at 100,000 cells per well and transfected in triplicate approximately 24 h later with 0.5 mg DNA per well using 400 ng Cripto/50 ng FAST2 (FoxH1)/25 ng A3-lux/25 ng CMV-b-galactosidase per well. Cells were treated approximately 24 h following transfection and then harvested approximately 16 h following treatment. Luciferase assays were performed as described for HepG2 cells described above.

Figure 6:
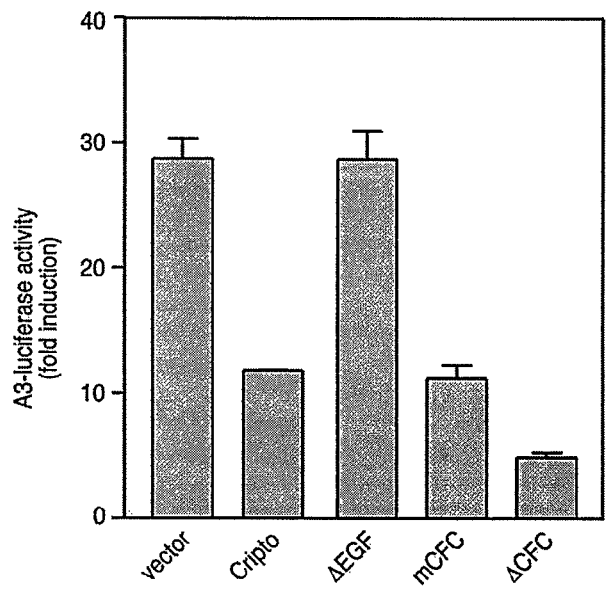
FIG. 6 shows the EGF-like domain of Cripto mediates antagonism of TGF-b signaling. 293T cells were transfected in triplicate with vector or the indicated Cripto constructs and A3-luciferase/FAST-2/CMV-b-galactosidase. Cells were treated with vehicle or with 100 pM TGF-$b_1$ and resulting luciferase activities were normalized relative to b-gal activities. Data were presented as fold increase in luciferase activities in TGF-$b_1$ treated cells relative to vehicle treated cells.

FIG. 6 shows that when 293T cells were transfected with empty vector or various Cripto constructs together with FAST2/A3-luciferase and then treated with 100 pM TGF-$b_1$, luciferase induction was reduced ~3-fold in cells transfected with wild type Cripto (FIG. 6, lane 2) but was unaffected in cells transfected with Cripto DEGF mutant (DEGF) (FIG. 6, lane 3) relative to induction of luciferase in cells transfected with empty vector (FIG. 6, lane 1). This result indicates that the EGF-like domain of Cripto is required for antagonism of TGF-$b_1$ signaling. In contrast, the mCFC mutant (H104G, W107G) blocked TGF-b signaling as effectively as wild type Cripto (FIG. 6, lane 4) while the Cripto DCFC mutant (DCFC) blocked TGF-b signaling even more effectively than wild type Cripto (FIG. 6, lane 5). Therefore, the CFC domain is not required for Cripto antagonism of TGF-b signaling but rather it may partially interfere with Cripto's ability to block TGF-b signaling as indicated by the fact that Cripto DCFC had a greater blocking effect than wild type Cripto. Together, these data indicate that the EGF-like domain of Cripto is both necessary and sufficient for inhibition of TGF-b signaling.

Figure 7:
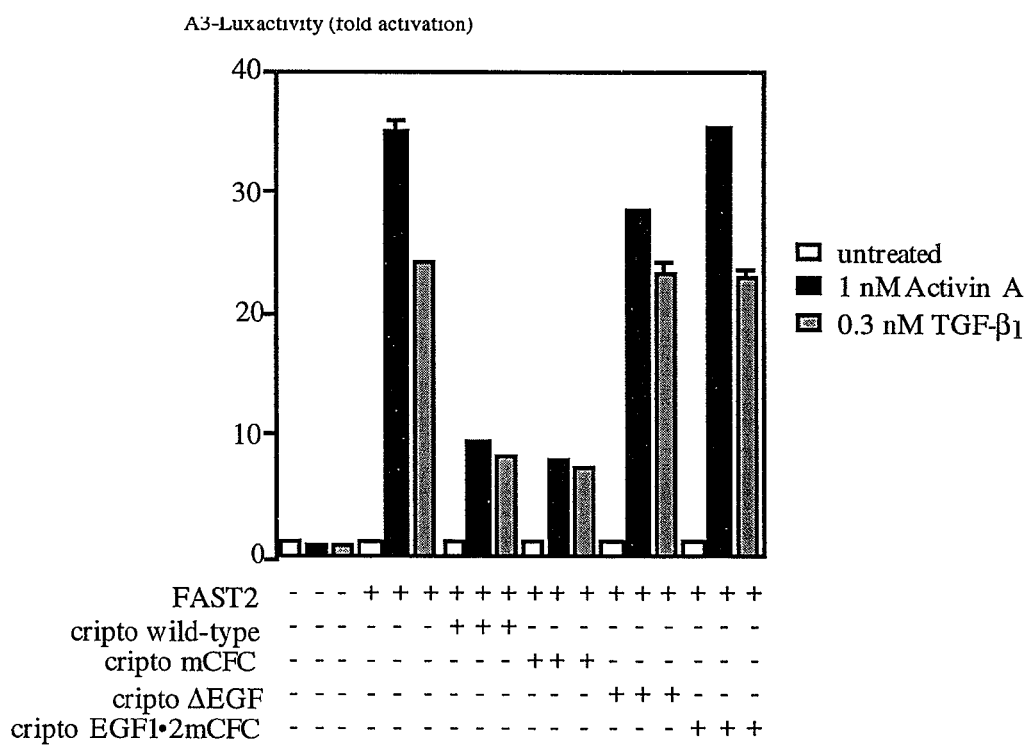
FIG. 7 shows the EGF-like domain of Cripto is required for antagonism of activin-A and TGF-$b_1$ signaling in 293T cells. 293T cells were transfected with the indicated constructs and then treated with vehicle or 1 nM activin-A or 0.3 nM TGF-$b_1$. Luciferase activities were normalized to b-galactosidase activities and data were presented as fold increase in luciferase activities relative to untreated cells

In another experiment, activin-A treatment caused a 30 to 40-fold and TGF-$b_1$ treatment caused an ~25 fold induction of luciferase expression in 293T cells which were blocked by wild type Cripto (FIG. 7). The ability of Cripto to block activin-B signaling was similar to its ability to block activin-A signaling in these cells (data not shown). Like wild type Cripto, the Cripto mCFC mutant blocked activin-A and TGF-$b_1$ signaling in these cells (FIG. 7). In contrast, neither the Cripto DEGF mutant with the EGF-like domain deleted nor the EGF1•2mCFC mutant were able to block activin-A or TGF-$b_1$ signaling in 293T cells (FIG. 7). These results indicate that the EGF-like domain of Cripto is required for antagonism of activin-A and TGF-b signaling.

Example 6

The CFC Domain of Cripto is not Required for TGF-b Binding

Figures 8A, 8B:
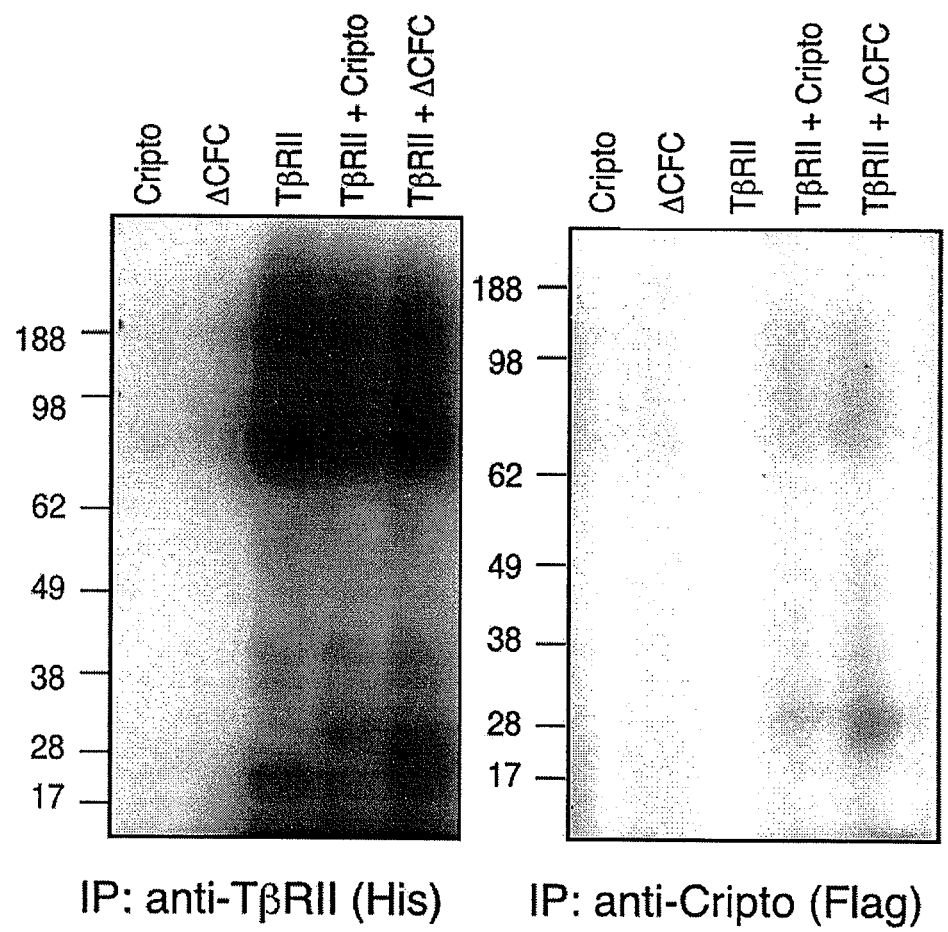
FIGS. 8A-B show the CFC domain of Cripto is not required for binding to TGF-b. 293T cells were transfected with the indicated constructs and subjected to crosslinking with [$^{125}$I]-TGF-$b_1$. Solubilized, crosslinked complexes were isolated by immunoprecipitation using anti-His antibody targeting TbRII (FIG. 8A) or anti-FLAG antibody targeting Cripto (FIG. 8B). Immunoprecipitated proteins were resolved by SDS-PAGE and visualized by autoradiography.

Having demonstrated that the Cripto DCFC mutant can block TGF-$b_1$ signaling, we next tested whether this mutant can bind and crosslink to TGF-$b_1$. 293T cells were transfected with wild type Cripto (FIG. 8, lane 1), Cripto DCFC (FIG. 8, lane 2), TbRII alone (FIG. 8, lane 3), TbRII and Cripto (FIG. 8, lane 4) or TbRII and Cripto DCFC (FIG. 8, lane 5). Cells were labeled with [$^{125}$I]-TGF-$b_1$ and subjected to covalent crosslinking followed by immunoprecipitation with an antibody directed against TbRII (anti-His, FIG. 8A) or against Cripto (anti-FLAG, FIG. 8B).

For covalent crosslinking studies, 293T cells were plated on six-well plates coated with polylysine at a density of 400,000 cells per well and then transfected approximately 24 h later. Cells were transfected with 4 mg DNA per well with ratios of 0.5 mg TbRII/0.5 mg ALK5/3 mg Cripto unless otherwise indicated for [$^{125}$I]-TGF-b1 crosslinking or 2 mg ActRII/1 mg Cripto/1 mg vector for [$^{125}$I]-activin-A crosslinking. As necessary, empty vector was used to keep the amount of DNA transfected constant at 4 mg. Covalent crosslinking was performed approximately 48 h after transfection by first washing cells in Hepes Dissociation Buffer (HDB) and then incubating them with [125I]-TGF-$b_1$ or [$^{125}$I]-activin-A in binding buffer (HDB containing 0.1% BSA, 5 mM $MgSO_4$ and 1.5 mM $CaCl_2$) at room temperature for approximately 4 h. Cells were then rinsed in HDB, incubated in HDB containing 0.5 mM disuccinylsuberate (DSS) for 30 min on ice, rinsed in HDB and then solubilized in lysis buffer (TBS containing 1% NP-40, 0.5% deoxycholate and 2 mM EDTA) for 1 h on ice. Solubilized, crosslinked complexes were incubated for approximately 24 h at 4° C. with 2 mg of either anti-FLAG (M2), anti-His or anti-myc antibodies. Immune complexes were precipitated using protein-G agarose and analyzed using SDS-PAGE and autoradiography.

As expected, anti-His antibody targeting TbRII did not precipitate labeled complexes from cells transfected with Cripto alone (FIG. 8A, lane 1) or Cripto DCFC alone (FIG. 8A, lane 2), but it did precipitate [$^{125}$I]-TGF-$b_1$-labeled TbRII from cells in which TbRII was transfected either alone (FIG. 8A, lane 3), or in which TbRII was co-transfected either with Cripto (FIG. 8A, lane 4) or Cripto DCFC (FIG. 8A, lane 5). In addition, a labeled Cripto complex of ~32 kDa was immunoprecipitated from cells co-transfected with TbRII and Cripto (FIG. 8A, lane 4) while a complex of ~28 kDa was precipitated from cells co-transfected with TbRII and Cripto DCFC. The latter complex was slightly larger than [$^{125}$I]-TGF-$b_1$ dimer of ~25 kDa (FIG. 8A, lane 5) and it was consistent with the predicted size of an [$^{125}$I]-TGF-$b_1$•DCFC complex.

We also precipitated labeled complexes with anti-FLAG antibody targeting Cripto and Cripto DCFC. When 293T cells were transfected with Cripto alone (FIG. 8B, lane 1) or Cripto DCFC alone (FIG. 8B, lane 2), crosslinked with [$^{125}$I]-TGF-$b_1$ and immunoprecipitated with an anti-FLAG antibody, no bands were observed. This result is consistent with the inability of Cripto and Cripto DCFC to bind TGF-b in the absence of TbRII. As predicted, transfection of TbRII alone followed by cell labeling, crosslinking and immunoprecipitation using anti-FLAG antibody did not result in observation of crosslinked complexes (FIG. 8B, lane 3). However, co-transfection of 293T cells with TbRII and Cripto (FIG. 8B, lane 4) or TbRII and Cripto DCFC (FIG. 8B, lane 5) led to precipitation of complexes of ~32 kDa and ~28 kDa representing the [$^{125}$I]-TGF-$b_1$•Cripto complex and the [$^{125}$I]-TGF-$b_1$•DCFC complex, respectively. This result provided further evidence that the CFC domain is not required for Cripto binding to TGF-b. In addition, a ~85 kDa band representing [$^{125}$I]-TGF-$b_1$•TbRII was present in each of these lanes (FIG. 8B, lanes 4, 5). Therefore, in the context of [$^{125}$I]-TGF-$b_1$ crosslinking, either an anti-TbRII antibody or an anti-Cripto antibody can precipitate complexes containing both labeled TbRII and labeled Cripto. This is similar to what is observed in crosslinking experiments with TbRII, [$^{125}$I]-TGF-$b_1$ and ALK5 in which the ligand mediates assembly of both Type II and Type I receptors into a stable complex.

Example 7

Mutation of Threonine 72 Blocks Cripto Antagonism of TGF-b and Activin Signaling It has previously been shown that Cripto is modified by O-fucosylation on a conserved threonine residue (Thr 72 in mouse Cripto, Thr 88 in human Cripto) within its EGF-like domain and that mutation of this threonine to an alanine blocks the ability of Cripto to bind nodal and facilitate nodal signaling. The EGF-like domain of Cripto plays an important role in facilitating nodal signaling, and results presented above indicate that it also plays an important role in blocking both TGF-$b_1$ and activin-A signaling. Therefore, we tested whether mutation of Thr 72 to Ala, which prevents fucosylation within this domain and blocks nodal signaling, might similarly interfere with Cripto's ability to block TGF-b and activin signaling.

Figure 9A:
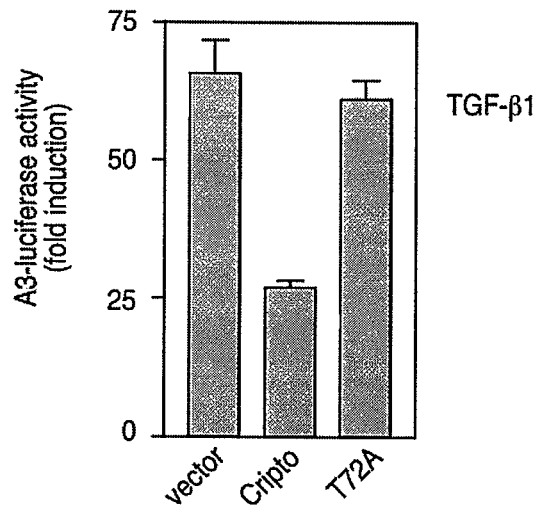
FIGS. 9A-C show Cripto T72A mutation disrupted the ability to block TGF-b and activin signaling. 293T cells were transfected in triplicate with vector, Cripto or Cripto mutant (T72A) and A3-luciferase/FAST-2/CMV-b-galactosidase. Cells were treated with vehicle or with 100 pM TGF-$b_1$ (FIG. 9A), 300 pM activin-A (FIG. 9B) or 300 pM activin-B (FIG. 9C) and resulting luciferase activities were normalized and presented as fold increase relative to b-galactosidase activities in vehicle-treated cells.
Figure 9B:
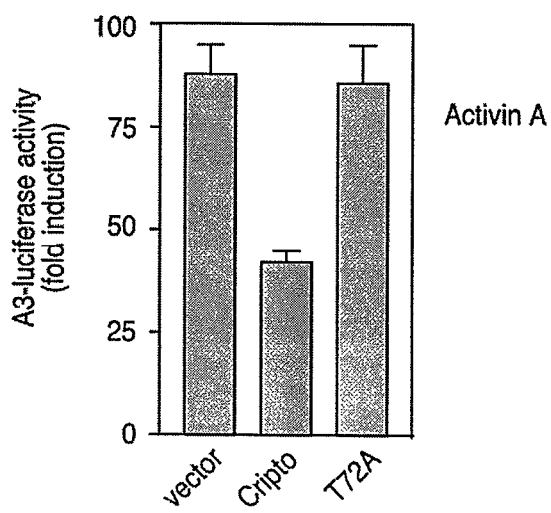
Figure 9C:
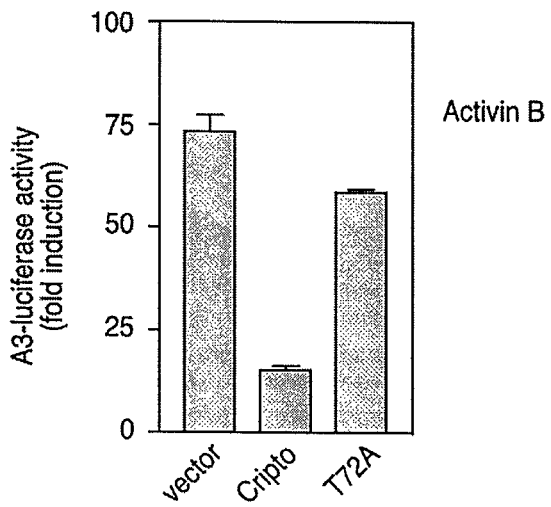

FIG. 9 shows the relative effects of wild type Cripto and the Thr 72→Ala (T72A) Cripto fucosylation mutant on TGF-$b_1$ (FIG. 9A), activin-A (FIG. 9B) and activin-B (FIG. 9C) signaling. 293T cells were transfected with empty vector, wild type Cripto or the Cripto (T72A) mutant together with FAST2/A3-luciferase. When 293T cells were treated with 100 pM TGF-$b_1$ (FIG. 9A), luciferase induction relative to vector-transfected cells (FIG. 9A, lane 1) was reduced in cells transfected with wild type Cripto (FIG. 9A, lane 2) but was unaffected in cells transfected with the Cripto (T72A) mutant (FIG. 9A, lane 3).

Similarly, when cells were treated with 300 pM activin-A, luciferase induction was blocked by wild type Cripto (FIG. 9B, lane 2) but not the Cripto (T72A) mutant (FIG. 9B, lane 3). Finally, when cells were treated with 300 pM activin-B, Cripto blocked luciferase induction consistent with our previous observations and those of others. However, unlike what was observed with TGF-b and activin-A, the Cripto (T72A) mutant could partially block activin-B signaling (FIG. 9C, lane 3). This is consistent with a previous report demonstrating that this mutant can bind activin-B and that the CFC domain of Cripto is important for Cripto antagonism of activin-B.

Example 8

The EGF-Like and CFC Domains of Cripto Both Participate in Blocking Activin-B Signaling In an attempt to clarify the functional importance of the EGF-like and CFC domains on Cripto antagonism of activin-A and activin-B signaling, 293T cells were transfected with empty vector, the Cripto DEGF mutant or the Cripto DCFC mutant together with FAST2/A3-luciferase and luciferase induction was measured in response to treatment with activin-A or activin-B. Consistent with previous observations, Cripto DEGF mutant did not block activin-A signaling (FIG. 10). In contrast, the Cripto DEGF mutant blocked roughly half of the luciferase activity induced by activin-B (FIG. 10), indicating an independent role for the CFC domain in blocking activin-B signaling. In contrast to the Cripto DEGF mutant, the Cripto DCFC mutant strongly blocked luciferase induction by either activin-A or activin-B (FIG. 10). Therefore, the EGF-like domain appears to be necessary and sufficient for antagonism of activin-A and TGF-$b_1$ signaling by Cripto while either the EGF-like domain or the CFC domain can apparently function independently to block signaling by activin-B.

Example 9

The CFC Domain of Cripto is not Required for Activin-A Binding

Having demonstrated that the CFC domain of Cripto is not required for inhibition of activin-A signaling, we next tested whether this domain is required for Cripto to bind activin-A and activin-B. 293T cells were transfected with Cripto (FIG. 11, lane 1); Cripto DCFC (FIG. 11, lane 2); ActRII (FIG. 11, lane 3); ActRII and Cripto (FIG. 11, lane 4); or ActRII and Cripto DCFC (FIG. 11, lane 5), subjected to labeling and crosslinking with [$^{125}$I]-activin-A or [$^{125}$I]-activin-B followed by immunoprecipitation with either an anti-myc antibody targeting ActRII (FIG. 11A) or an anti-FLAG antibody targeting Cripto and Cripto DCFC (FIG. 11B).

As predicted, transfection of Cripto alone (FIG. 11A, lane 1) or Cripto DCFC alone (FIG. 11A, lane 1) followed by cell labeling, crosslinking and immunoprecipitation using an antibody targeting ActRII did not result in detection of crosslinked complexes. However, transfection of 293T cells with ActRII alone (FIG. 11A, lane 3) resulted in bands at ~80 kDa representing the [$^{125}$I]-activin-A•ActRII complex and bands at ~28 kDa representing the [$^{125}$I]-activin-A dimer. Co-transfection of ActRII and Cripto (FIG. 11A, lane 4) or ActRII and Cripto DCFC (FIG. 11A, lane 5) led to precipitation of additional complexes of ~34 kDa and ~30 kDa likely representing the [$^{125}$I]-activin-A•Cripto complex and [$^{125}$I]-activin-A•DCFC complex, respectively. In parallel experiments, we have been unable to detect crosslinked complexes with [$^{125}$I]-activin-B, apparently due to loss of binding activity resulting from the iodination procedure.

We also precipitated [$^{125}$I]-activin-A labeled complexes with anti-FLAG antibody targeting Cripto and Cripto DCFC. When 293T cells were transfected with Cripto alone or Cripto DCFC alone, crosslinked with [$^{125}$I]-activin-A and then subjected to immunoprecipitation with anti-FLAG antibody, no bands were observed (FIG. 11B). This result is similar to what was observed with TGF-b crosslinking (FIG. 8), suggesting that when transfected alone Cripto and Cripto DCFC are each unable to bind activin-A. As predicted, transfection of ActRII alone followed by cell labeling, crosslinking and immunoprecipitation using anti-FLAG antibody did not result in observation of crosslinked complexes (FIG. 11B, lane 3). Co-transfection of 293T cells with ActRII and Cripto (FIG. 11B, lane 4) or ActRII and Cripto DCFC (FIG. 11B, lane 5) led to precipitation of complexes of ~34 kDa and ~30 kDa representing the [$^{125}$I]-activin-A•Cripto complex and the [$^{125}$I]-activin-A•DCFC complex, respectively, providing evidence that the CFC domain is not required for binding of Cripto to activin-A. Rather, consistent with functional data, the Cripto DCFC mutant appears to bind and crosslink to [$^{125}$I]-activin-A more effectively than wild type Cripto as indicated by their relative band intensities (FIG. 11B, lanes 4, 5). The ~80 kDa band representing [$^{125}$I]-activin-A•ActRII was present in each of these lanes (FIG. 11B, lanes 4, 5) indicating that in the presence of activin-A, Cripto and Cripto DCFC each can form a stable complex with ActRII.

Example 10

Cripto Antagonizes Activin-A/TGF-$b_1$ but Facilitates Nodal Signaling in 293T Cells The effects of Cripto on activin-A and TGF-$b_1$ signaling as opposed to nodal signaling were compared. It has previously been shown that transfection of nodal and Cripto into 293T cells resulted in secretion of processed nodal protein that generates signals in the cells producing it. Thus 293T cells were transfected with FAST2, the A3-luciferase reporter plasmid and various amounts of Cripto DNA. The cells were then treated with activin-A or TGF-$b_1$ or co-transfected with a mouse nodal expression vector.

Figure 12:
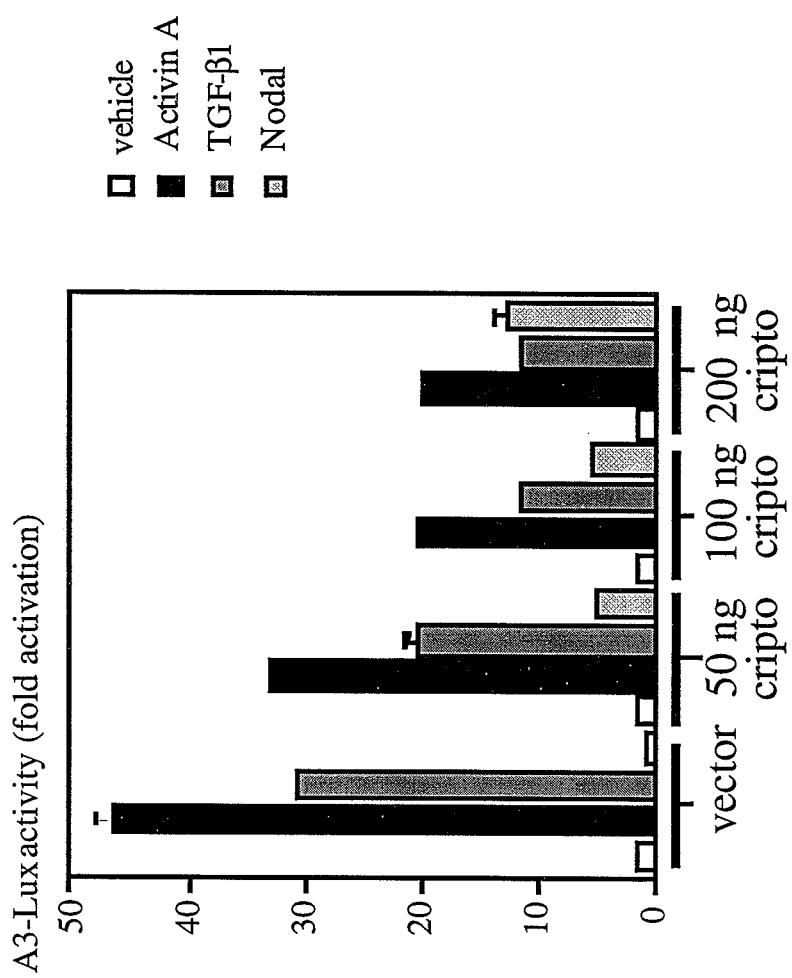
FIG. 12 shows Cripto antagonizes activin/TGF-b but facilitates nodal signaling in 293T cells. 293T cells were transfected with either empty vector or nodal and the indicated amount of Cripto DNA as previously described (Gray et al., 2003) and then treated as indicated with 1 nM activin-A or 0.3 nM TGF-$b_1$. Luciferase values were normalized to b-galactosidase activities and data were presented as fold increase in luciferase activities relative to untreated cells.

FIG. 12 shows that in the absence of Cripto, activin-A treatment induced luciferase expression ~45 fold relative to untreated cells and TGF-$b_1$ treatment induced luciferase expression ~30 fold. Co-transfection with increasing amounts of Cripto DNA caused a dose-dependent blockade of activin-A and TGF-$b_1$ signaling. Conversely, nodal did not generate a detectable signal in the absence of Cripto but its signaling increased as the amount of Cripto DNA transfected into the cells was increased (FIG. 12). Therefore, Cripto can have opposing effects on activin/TGF-b as opposed to nodal signaling despite the fact that activin and nodal utilize the same signaling receptors and each of these ligands signal via the Smad2/3 pathway.

Example 11

Regulation of TGF-b Superfamily Signaling by Cripto

FIG. 13 illustrates proposed mechanisms by which Cripto either facilitates nodal and Vg1/GDF1 signaling (FIG. 13A) or inhibits TGF-b and activin signaling (FIG. 13B). Cripto binds nodal or Vg1/GDF1 and ALK4 and allows these ligands to assemble type II and type I receptors to elicit signaling responses such as mesendoderm induction during vertebrate embryogenesis (FIG. 13A).

In contrast to its effects on nodal signaling, Cripto binds activin-A in the presence of its type II receptors and antagonizes activin signaling. Cripto also inhibits activin-B signaling, although the mechanism of this antagonism appears to differ from that of activin-A. Cripto also binds TGF-$b_1$ in the presence of TbRII and blocks TGF-$b_1$ signaling, demonstrating a mechanism of antagonism similar to that on activin-A signaling (FIG. 13B). Type II receptor binding is required for activin-A and TGF-$b_1$ to form complexes with either type I receptors or Cripto, and crosslinking data presented herein indicate that Cripto may disrupt the ability of activin-A and TGF-$b_1$ to form functional complexes with type I receptors (FIG. 13B). The ability of Cripto to inhibit TGF-$b_1$ and activins, which are tumor suppressors and can potently inhibit cell growth, provides a mechanism by which it could promote tumorigenesis.

Example 12

Inhibition of Activin•Cripto or TGF-b•Cripto Complexes Formation

It is hypothesized that antagonism of activin and TGF-b signaling by Cripto can be disrupted using antibodies directed against Cripto. Binding of these antibodies to Cripto is predicted to disrupt the ability of Cripto to bind to activin or TGF-b, thereby reversing the antagonism of activin and TGF-b signaling by Cripto.

Cripto has two highly conserved domains, the EGF-like domain and the CFC domain, that have been shown to be functionally important and are involved in protein-protein interactions. The EGF-like domain of Cripto binds directly to the TGF-b superfamily member nodal and related ligands Vg1 and GDF1 to facilitate signaling via activin receptors ActRII/IIB and ALK4. The EGF-like domain of Cripto is required for antagonism of activin and TGF-b signaling. Deletion of the EGF-like domain (DEGF) resulted in a Cripto mutant with undetectable activin binding in cross-linking assays and an inability to block activin or TGF-b signaling. Therefore, it is proposed that, similar to nodal, activin and TGF-b bind to the EGF-like domain of Cripto and this domain represents a primary target for antibody blockade of Cripto antagonism of activin and TGF-b.

It has also been shown that the CFC domain of Cripto binds directly to ALK4 and, similar to the EGF-like domain, this domain is required for nodal signaling. We have tested a Cripto mutant with two point mutations in the CFC domain that was previously shown to be defective in ALK4 binding and nodal signaling. This mutant, called mCFC, bound activin in crosslinking assays when co-expressed with activin type II receptors (ActRII/IIB) and blocked activin signaling when transiently transfected into 293T cells. This is consistent with activin binding to the EGF-like domain of Cripto. Consequently, antibodies that can disrupt Cripto binding to ALK4 may have effects on Cripto antagonism of activin and TGF-b. Recently it was shown that monoclonal antibodies targeting either the CFC domain (Adkins et al., 2003) or EGF-like domain (Xing et al., 2004) of Cripto can inhibit tumor growth in vivo.

Antibodies can be generated against recombinant soluble Cripto protein (containing both the EGF-like and CFC domains) purified from mammalian cells or a synthetic peptide spanning the EGF-like domain of Cripto. Raising antibodies against the full-length soluble Cripto protein will enable us to test the effects of antibodies targeting both the EGF-like and CFC domains.

Soluble Cripto with a C-terminal. FLAG epitope tag can be expressed in mammalian cells (293T cells or CHO cells) following transient transfection. Cells stably expressing soluble Cripto-FLAG can be generated by selection in G418 for larger-scale production of protein. Medium containing soluble Cripto-FLAG can be enriched using FLAG-agarose immunoaffinity chromatography and purified by reverse-phase HPLC. The Cripto EGF-like domain can also be generated as a synthetic peptide to be used as an antigen to generate anti-Cripto antibodies. Peptide spanning the human Cripto EGF-like domain has previously been synthesized, refolded and shown to have biological activity. A similar polypeptide spanning the mouse Cripto EGF-like domain can be generated using mouse Cripto sequence generally available in the art.

Initially, potential neutralizing anti-Cripto antibodies can be tested at various doses for their ability to disrupt Cripto antagonism of activin-A, activin-B and TGF-$b_1$ signaling in 293T cells. The ability of activin-A, activin-B and TGF-$b_1$ to induce luciferase can be measured in cells transfected with Cripto, FAST2 and A3-luciferase constructs. The effects of the anti-Cripto antibodies can be compared to normal rabbit serum (NRS). If antibodies directed against full-length Cripto or peptide containing the EGF-like domain are found to block Cripto effects on activin and TGF-b signaling in 293T cells, further testing can be performed using other cells including breast epithelial and breast cancer cell lines.

Alternatively, antagonistic activities of Cripto may be inhibited by molecules that bind to Cripto, thereby disrupting the ability of Cripto to bind to activin or TGF-b. For example, Lefty and Tomoregulin have each been shown to bind directly to Cripto and have been shown to block nodal signaling (nodal signaling requires Cripto). The prediction is that by binding to Cripto they might interfere with Cripto's ability to bind to TGF-b/activin thereby blocking Cripto's effects on these ligands.

Example 13

Inhibition of Activin•Cripto or TGF-b•Cripto Complexes Formation by Soluble Mutated Activin Receptor-Like Kinases-4 (ALK-4)

The aim here is to generate a soluble version of the ALK4-extracellular domains (ECD) that is capable of binding Cripto but not a TGF-b superfamily ligand such as activin. It is hypothesized that such a protein will not bind directly to a TGF-b superfamily ligand and interfere with signaling, but rather will have the ability to bind Cripto and disrupt the ability of Cripto to block activin or TGF-b binding and signaling.

The functional binding site for activin on ALK4 has been identified recently (Harrison et al., 2003). It was demonstrated that I70A, L75A and P77A ALK4-ECD mutants were unable to bind activin or mediate activate signaling. It was concluded that I70, L75 and P77 are central to the activin binding site on the ALK4-ECD. Although mutating one of these residues is sufficient to disrupt activin•ALK4 binding, soluble: versions of ALK4-ECD incorporating these mutations individually, in pairs or incorporating all three mutations can also be generated.

The soluble ALK4 ECD proteins incorporating the I70A, L75A and/or P77A mutations and a C-terminal FLAG epitope tag can be expressed in mammalian cells (293T cells or CHO cells) following transient transfection. Cells stably expressing soluble ALK4-ECD-FLAG proteins will be generated by selection in G418 for larger-scale production of protein. Medium containing soluble ALK4-ECD-FLAG proteins can be enriched using FLAG-agarose immunoaffinity chromatography and purified by reverse-phase HPLC.

Initially, soluble ALK4 ECD proteins incorporating the I70A, L75A and/or P77A mutations can be tested at various doses for their ability to disrupt Cripto antagonism of activin-A, activin-B and TGF-$b_1$ signaling in 293T cells. The ability of activin-A, activin-B and TGF-$b_1$ to induce luciferase will be measured in cells transfected with Cripto, FAST2 and A3-luciferase constructs. The mutant ALK4-ECD proteins will be compared to wild type soluble ALK4-ECD. The effects of these ALK4-ECD proteins on activin signaling in the absence of Cripto will also be tested to determine if they interfere with activin signaling. In addition to 293T cells, other cells including breast epithelial and breast cancer cell lines can also be used.

Example 14

Inhibition of Cripto Expression

Multiple strategies can be pursued to prevent Cripto antagonism of activin and TGF-b signaling in a defined in vitro system. Useful strategies include, but are not limited to, disruption of Cripto expression by homologous recombination, the previously validated Cripto antisense vector approach, and Cripto RNA interference.

Homologous Recombination

Disruption of Cripto expression by homologous recombination in mouse embryonic stem cells has been previously described (Ding et al., 1998). It was shown that mice lacking both alleles of Cripto died very early during embryogenesis probably due to a loss of nodal signaling which requires Cripto. However, the effects of deleting one Cripto allele or of disrupting both alleles in the adult in specific tissues (i.e. conditional knockout) remains to be evaluated in terms of effects on cancer susceptibility.

Antisense Oligonucleotides

The use of antisense oligonucleotides to disrupt Cripto expression has also been described (Niemeyer et al., 1998). Retroviral vector was used to deliver Cripto antisense RNA to mouse mammary CID-9 cells. Reduction of endogenous Cripto expression in these cells via expression of an antisense Cripto vector construct decreased cell proliferation while overexpression of Cripto led to increased cell growth. Antisense inhibitors of Cripto also led to loss of transformed phenotype in colon carcinoma cells (Ciardiello et al., 1994).

Niemeyer et al. (1998) used the retroviral vector pGCEN containing the antisense Cripto sequence to infect CID-9 cells and generated cells stably expressing the antisense construct. Similar approach can be performed with the retroviral pCLNC vector, which was used previously to infect cells and generate stable lines (Gray and Vale, unpublished data). One of ordinary skill in the art would recognize that other vectors besides retroviral vectors can also be used according to standard procedures in the art. In one example, mouse Cripto sequence can be subcloned into the pCLNC vector in the antisense or the sense orientation. These constructs or empty pCLNC vector are used to generate virus, infect CID-9 cells and obtain G418 resistant cells. The effectiveness of this approach in increasing or decreasing Cripto can be measured directly by examining Cripto expression in the resulting G418 resistant cells by Western blot with anti-Cripto antibodies.

The effects of activin and TGF-b and their antagonists on the proliferation of CID-9 cell (or other target cells well-known in the art) can be measured using protocols generally available to one of ordinary skill in the art. For example, the CyQUANT® cell proliferation assay kit (Invitrogen) can be used according to manufacturer's instructions. The sensitivity of a target cell line to growth inhibition by activin and TGF-b and their antagonists can be established by treating a range of cells with a range of doses of each ligand, antagonist or vehicle and testing the effects on proliferation over time. Once the effects of activin, TGF-b or antagonist on the parental cells are established, these experiments can be repeated on cells stably expressing the retroviral vector, Cripto-sense or Cripto-antisense retroviral DNA and compare the resulting effects of various doses of activin and TGF-b on cell proliferation. It has been shown that Cripto overexpression conferred anchorage independent growth capability on CID-9 cells. Therefore, in addition to measuring the proliferation rate of Cripto over- and under-expressing cells in monolayer culture, the ability of these cells to grow in soft agar will also be measured. Similar experiments can be performed on cells stably overexpressing RNAi vectors (as described below).

RNA Interference

The principle of RNA interference is the abrogation of target gene expression initiated by small interfering RNA (siRNA) homologous in sequence to the gene to be silenced (Elbashir et al., 2001). Recently, it was shown that transfection of a synthetic 21-nucleotide siRNA duplexes could specifically suppress expression of endogenous and heterologous genes in different mammalian cell lines. Viral infection of target cells such as CID-9 cells to express a 21-nucleotide siRNAs targeted against Cripto can be performed using the U6 promoter system based on the pSilencer vector (Ambion) and/or the polymerase III HI-RNA promoter (pSUPER) (Brummelkamp et al., 2002). These RNAs require a 5' UU overhang to bind their target genes. Therefore, target sequences for siRNAs will be identified by scanning the Cripto gene for sequences containing AA targets complementary to the siRNA UU overhang. The AA and downstream 19 nucleotides will be compared to an appropriate genome database to eliminate sequences with significant homology to other genes. Sequences that are specific to the mouse Cripto gene and are common between mouse, rat, and human Cripto will be initial siRNA targets.

Retroviral and/or lentivirus vectors (provided by Dr. Inder Verma, The Salk Institute) will be used for the infection and stable expression of siRNAs in CID-9 cells. These vectors can be designed to contain either a polymerase III HI-RNA promoter or a U6 small nuclear RNA promoter to continuously drive high levels of siRNA expression in target cells. Cripto-specific inserts can be designed such that the specified 19-nucleotide sequence of Cripto is separated by a short spacer from the reverse complement of the same 19-nucleotide sequence. The resulting transcript is predicted to fold back on itself to form a 19 base pair hairpin-loop structure necessary for siRNA function. Expression of Cripto siRNAs using these two vector systems will allow for efficient Cripto disruption.

In addition to validating this approach in cultured mouse CID-9 cells, deliverance of siRNA or antisense RNA targeting Cripto expression by retroviral or lentiviral vectors represents a potential gene therapy approach to treat human cancer.

Example 15

Augmenting Smad2/3 Signaling Using Mutant Activin

Another method of overcoming the antagonistic effects of Cripto on activin and TGF-b signaling (i.e. Smad2/3 signaling) is to design a mutant form of activin (or possibly TGF-b) that retains signaling activity but is unable to bind Cripto. Such a mutant ligand may have therapeutic value since it will be capable of activating Smad2/3 signaling in tissues in which signaling by wild type activin and TGF-b is otherwise suppressed by Cripto.

Cripto-Resistant Activin

In an effort to identify receptor-binding residues on activin-A, a rapid functional screen for expressing and characterizing activin-A and activin-A mutants has been established using 293T cells. This system incorporates FAST2 and A3-luciferase and is based on a system originally developed to characterize nodal and Cripto signaling. Full-length activin bA cDNA has been expressed in 293T cells and dimeric, processed activin-A was secreted into the medium. When conditioned medium from these cells was used to treat separate 293T cells transfected with A3-luciferase and FAST2, luciferase reporter expression was induced, indicating the secreted activin-A was fully active.

Using the above system, several activin-A mutants were generated and quantitated from conditioned medium by Western blot analysis. We have confirmed previous results indicating that mutation of Lys 102 to Glu (K102E) disrupts activin-A activity. However, most of the mutants we have generated appear to retain full activity. We now propose to compare the ability of transfected Cripto to antagonize wild type activin-A signaling in 293T cells with its ability to antagonize these activin-A mutants. The goal is to identify activin-A mutants that are resistant to Cripto antagonism relative to wild type activin-A. Additional activin-A alanine substitution point mutants can be generated with the aim of identifying activin-A mutants with Cripto full signaling activity and Cripto resistance.

Example 16

Constructs and Uses of Soluble and Membrane-Bound Cripto

Cripto is expressed at high levels in tumors and has been shown to promote tumorigenesis, whereas TGF-b and activin are tumor suppressors and potently inhibit cell proliferation. Paradoxically, TGF-b/activin can also promote tumorigenesis at later stages of tumor progression when tumor cell proliferation is no longer inhibited by TGF-b/activin signaling. At these later stages, TGF-b and activin are produced at high levels by tumor cells and signaling of these ligands causes angiogenesis, immunosuppression and epithelial to mesenchymal transition which favor tumor growth and spread. Therefore, it may be of therapeutic value to either facilitate TGF-b/activin signaling or to block TGF-b/activin signaling depending on the context (i.e. stage of tumor progression).

Blocking TGF-b/activin signaling may have therapeutic benefit in several contexts including, but are not limited to, cancer, wound healing and liver regeneration. As mentioned above, during later stages of tumorigenesis tumor cells secrete TGF-b and activin that cause effects favoring further tumor growth and metastasis due to their effects on blood vessels, cells of the immune system and organs which are targets for metastasis. Directing Cripto expression or administering soluble forms of Cripto to these sites may help to slow tumor progression.

TGF-b and activin accelerate wound healing but they also can cause excessive extracellular matrix deposition and unwanted scarring. Cripto may therefore have utility as a modulator of TGF-b/activin in this context. With regard to liver regeneration, TGF-b and activin are potent antiproliferative agents in liver and therefore blocking their signaling with Cripto may prove useful in facilitating liver regeneration.

Design of Cripto Mutants

Examples of Cripto constructs are indicated in FIG. 14. Initially, all constructs can be generated in mammalian expression vector such as pcDNA3 using standard PCR-based mutagenesis and subcloning techniques.

Cell-attached Cripto constructs can incorporate Cripto signal peptide with an in-frame epitope tag sequence (e.g. FLAG or His) immediately downstream of the signal peptide followed by the indicated Cripto sequences (FIG. 14), hydrophobic C-terminal domain required for GPI attachment and a stop codon. The Epidermal Growth Factor-Cripto, FRL-1, Cryptic (EGF-CFC) region of mouse Cripto (aa 60-134) has been shown to be sufficient to reconstitute one-eyed pinhead (oep) signaling in zebrafish embryos. This region can be expressed as a cell-attached protein and tested for its ability. to bind activin and TGF-b and antagonize their signaling (FIG. 14).

The EGF-like domain of mouse Cripto spans residues 60-95 (FIGS. 14-15) and deleting this region abolishes the ability of Cripto to bind activin-A as well as its ability to antagonize both activin-A and TGF-$b_1$ signaling. Cell-attached EGF-like domain construct can be tested for its effects on activin-A and TGF-$b_1$ binding and signaling. The effects of the GPI-anchored CFC domain (aa 99-134) on activin-A and TGF-$b_1$ binding and signaling can also be tested.

The functional role of individual amino acid in the Cripto EGF-like and CFC domains for activin-A and TGF-$b_1$ binding can be determined as follows. Mutants such as Cripto mCFC (H104G, W107G), which has two point mutations within the CFC domain and does not bind ALK4, and Cripto DEGF, which has the entire. EGF-like domain deleted and is unable to bind the TGF-b/activin-related ligand nodal, have been described above. Mutant Cripto EGF1•2mCFC, which blocks Cripto binding to activin and prevents Cripto antagonism of activin and TGF-b signaling, incorporates mEGF1, mEGF2 and mCFC tandem point mutations (N69G, T72A, R88G, E91G, H104G, W107G) (see FIGS. 14-15). The effects of these mutations, individually or in combination, can be tested by incorporating these or the corresponding alanine mutations into cell-attached or soluble Cripto constructs. For example, overlapping PCR mutagenesis can be used to generate these point mutations in full-length, GPI-anchored Cripto background. Similar mutations can also be generated in soluble EGF-like and CFC domain constructs.

Furthermore, there are 14 highly conserved residues in the EGF-like domain and 9 highly conserved residues in the CFC domain (FIG. 15). Fifteen of these conserved residues have previously been targeted for mutagenesis in the context of soluble mouse Cripto and characterized with respect to their ability to reconstitute one-eyed pinhead (oep) signaling in zebrafish embryos lacking both maternal and zygotic expression of oep (MZoep). RNA encoding soluble mouse Cripto or soluble EGF-CFC region could restore normal embryonic development as could the soluble Pro52, Phe85, His92, Arg95 and Glu97 Cripto Ala-substituted mutants (Minchiotti et al., 2001). Injected RNA encoding the Gly71Asn or the Phe78Ala mutants was unable to rescue the MZoep phenotype even at high doses while the Asn63, Ser77, Arg88, Glu91, His104, Leu114, Leu114, Leu122 and Arg116 Ala substituted mutants resulted in intermediate effects (Minchiotti et al., 2001). Each mutant was expressed in 293T cells and it was shown that with the exception of the Arg88Ala mutant, each of the fifteen mutants was expressed at approximately wild type levels (Minchiotti et al., 2001). To more fully characterize the activin and TGF-b binding site(s) on Cripto, similar study can be done with Ala substituted mutants in the context of full-length, GPI-anchored Cripto constructs or soluble Cripto constructs. It is expected that conserved residues within the EGF-like domain may constitute the activin and TGF-b binding surfaces.

It has been previously shown that Cripto can facilitate nodal signaling and activate mitogenic MAPK and PI3K pathways when present as a soluble protein, raising the possibility that Cripto may act both cell autonomously and as a secreted, soluble factor. Thus it is of interest to test the ability of several soluble Cripto constructs to bind activin and TGF-b and antagonize their signaling. Examples of soluble Cripto constructs are illustrated in FIG. 14. It has been previously shown that the C-terminal hydrophobic domain of Cripto is required for GPI-attachment and deletion of this domain results in secretion of soluble Cripto protein. Therefore, soluble Cripto constructs will incorporate this C-terminal deletion in addition to an in-frame C-terminal FLAG epitope tag followed by a stop codon (FIG. 14).

The following references are cited herein:

Adkins et al., Antibody blockade of the Cripto CFC domain suppresses tumor cell growth in vivo. *J. Clin. Invest.* 112:575-87 (2003).

Brummelkamp et al., A system for stable expression of short interfering RNAs in mammalian cells. *Science* 296:550-3 (2002).

Ciardiello et al., Inhibition of CRIPTO expression and tumorigenicity in human colon cancer cells by antisense RNA and oligodeoxynucleotides. *Oncogene* 9:291-8 (1994).

Ding et al., Cripto is required for correct orientation of the anterior-posterior axis in the mouse embryo. *Nature* 395: 702-7 (1998).

Elbashir et al., Duplexes of 21-nucleotide RNAs mediate RNA interference in cultured mammalian cells. *Nature* 411:494-8 (2001).

Gray et al., Cripto forms a complex with activin and type II activin receptors and can block activin signaling. *Proc. Natl. Acad. Sci. USA.* 100:5193-8 (2003).

Harrison et al., Identification of a functional binding site for activin on the type I receptor ALK4. *J. Biol. Chem.* 278:21129-35 (2003).

Minchiotti et al., *Development* 128:4501-10 (2001).

Niemeyer et al., Cripto: roles in mammary cell growth, survival, differentiation and transformation. *Cell Death Differ.* 5:440-9 (1998).

Xing et al., *Cancer Res.* 64:4018-23 (2004).

Yeo and Whitman, *Mol. Cell* 7:949-57 (2001).

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

---

What is claimed is:

1. A method of selectively inhibiting activin-B signaling, the method comprising administering a Cripto mutant that lacks the EGF domain or has a mutation of the threonine residue that is the site of fucosylation of the EGF domain.

2. The method of claim 1, wherein the Cripto mutant is a soluble Cripto mutant.

3. The method of claim 1, wherein the Cripto mutant is bound to a cell surface.

4. The method of claim 1, wherein the Cripto mutant is a human Cripto protein.

5. The method of claim 4, wherein the human Cripto protein comprises a deletion of KELNRTCCLNGGTCM-LGSFCACPPSFYGRNCEHDVR (amino acid residues 76 to 111 of SEQ ID NO:2).

6. The method of claim 4, wherein the human Cripto protein comprises a T88A amino acid mutation.

7. The method of claim 4, wherein the human Cripto protein comprises a mutation of the threonine residue at amino acid position 88 and further comprises a mutation at one or more amino acid positions selected from the group consisting of amino acid position 85, 104, 107, 120, or 123.

8. The method of claim 7, wherein the human Cripto protein has a mutation of the threonine residue at amino acid position 88 and further comprises mutations at amino acid positions 85, 104, 107, 120, and 123.

9. The method of claim 8, wherein the human Cripto protein comprises T88A, N85G, R104G, E107G, H120G, and W123G amino acid mutations.

10. The method of claim 1, wherein the Cripto mutant is a mouse Cripto protein.

11. The method of claim 10, wherein the mouse Cripto protein comprises a deletion of KSLNKTCCLNG-GTCILGSFCACPPSFYGRNCEHDVR (amino acid residues 60 to 95 of SEQ ID NO:1).

12. The method of claim 10, wherein the mouse Cripto protein comprises a T72A amino acid mutation.

13. The method of claim 10, wherein the mouse Cripto protein comprises a mutation of the threonine residue at amino acid position 72 and further comprises a mutation at one or more amino acid positions selected from the group consisting of amino acid position 69, 88, 91, 104, or 107.

14. The method of claim 13, wherein the mouse Cripto protein has a mutation of the threonine residue at amino acid position 72 and further comprises mutations at amino acid positions 69, 88, 91, 104, and 107.

15. The method of claim 14, wherein the mouse Cripto protein comprises T72A, N69G, R88G, E91G, H104G, and W107G amino acid mutations.

16. The method of claim 1, wherein the Cripto mutant comprises the CFC domain of Cripto.

17. The method of claim 1, wherein the Cripto mutant further comprises an epitope tag.

18. The method of claim 17, wherein the epitope tag is FLAG or His.

19. The method of claim 18, wherein the Cripto mutant further comprises a signal peptide.

20. The method of claim 1, wherein the Cripto mutant is administered to a male subject to disrupt spermatogenesis.

* * * * *